United States Patent [19]

Paradiso et al.

[11] Patent Number: 5,223,254
[45] Date of Patent: Jun. 29, 1993

[54] RESPIRATORY SYNCYTIAL VIRUS: VACCINES

[75] Inventors: Peter R. Paradiso, Pittsford; Stephen W. Hildreth, Rochester; Branda T. Hu; Antonia Martin-Gallardo, both of Pittsford; Rasappa Arumugham, West Henrietta, all of N.Y.

[73] Assignee: Praxis Biologics, Inc., Rochester, N.Y.

[21] Appl. No.: 247,017

[22] Filed: Sep. 20, 1988

Related U.S. Application Data

[63] Continuation-in-part of Ser. No. 102,180, Sep. 29, 1987, abandoned.

[51] Int. Cl.$^5$ .......................................... A61K 39/155
[52] U.S. Cl. .......................................... 424/89; 514/2; 514/8; 514/12
[58] Field of Search ............... 530/350, 395, 324, 325, 530/808, 826; 424/88, 89; 514/2, 8, 12; 536/23; 435/243, 320

[56] References Cited

PUBLICATIONS

Walsh, E. E. et al. Jun. 1987, Journal of Infectious Diseases 155(6):1198-1204, "Immunization with Glycoprotein Subunits of . . . ".
Wertz, G. W. et al. Journal of Virology 61(2):293-301, Feb. 1987, "Expression of the Fusion Protein of Human Respiratory Syncytial . . . ".
Elango, N. et al. 1985, Nucleic Acids Res. 13(5):1559-1574, "R.S.V. Fusion Glycoprotein: Nuecleotide Sequence of mRNA . . . ".
Trudel, M. et al. 1987, J. General Virology 68:2273-2280, "Identification of a Synthetic Peptide as Part of a Major . . . ".
Walsh, E. E. et al. 1985, J. General Virology 66:409-415, "Purification and Characterization of the R.S.V. Fusion Proteins".
Fundamental Virology, Raven Press, New York, N.Y. 1985 "Immunization Against Viruses".
Progress Towards Better Vaccines, R. Bell, et al. (editor) Oxford Univ. Press 1986.
Fernie and Gerin, 1982, Infect. Immun. 37: 243-24.
Wright et al., 1982, Infect. Immun. 37: 397-400.
Walsh and Hruska, 1983, J. Virol. 47: 171-177.
Walsh et al., 1984, J. gen. Virol. 65: 761-767.
Trudel et al., 1986, Can. J. Microbiol. 32: 15-21.
Taylor et al., 1984, Immunol. 52: 137-142.
Fernie et al., 1985, J. gen. Virol. 66: 1983-1990.
Mufson et al., 1985, J. gen. Virol. 66: 2111-2121.
Anderson et al., 1986, J. Clin. Microbiol. 23: 475-480.
Giminez et al., 1986, J. gen. Virol. 67: 863-970.
Samson et al., 1986, J. gen. Virol. 67: 1479-1483.
Murphy et al., Biol. Abst. 82(9) Nov. 1, 1987 Abstract No. 82912.
Walsh et al., 1986, J. gen. Virol. 67: 505-512.
Routledge et al., 1986, J. gen. Virol. 67: 2059-2064.
Watt et al., 1986, Clin. Exp. Immunol. 64: 503-509.
Olmsted et al., 1986, Proc. Nat'l. Acad. Aci. USA 83: 7462-7466.
Norrby et al., 1986, J. gen. Virol. 67: 2721-2729.
Murphy et al., 1986, J. Clin. Microbiol. 24: 197-202.
Norrby et al., 1987, Proc. Nat'l. Acad. Sci. USA 84: 6572-6576.
Walsh et al., 1987, J. gen. Virol. 68: 2169-2176.
Stott et al., 1987 J. Virol. 61: 3855-3861.

(List continued on next page.)

*Primary Examiner*—Christine M. Nucker
*Assistant Examiner*—T. Cunningham
*Attorney, Agent, or Firm*—Alan M. Gordon; Geraldine F. Baldwin

[57] ABSTRACT

Polypeptides, nucleotides, and compositions useful for preparing diagnostic reagents for and vaccines against human Respiratory Syncytial Virus are disclosed. The polypeptides include short polypeptides which are related to a neutralizing and fusion epitope of the Respiratory Syncytial Virus fusion protein or a neutralizing epitope of the G protein.

3 Claims, 11 Drawing Sheets

PUBLICATIONS

Trudel et al., 1987, Can. J. Microbiol. 33: 933–938.

Johnson et al., 1987, Proc. Nat'l. Acad. Sci. USA 84: 5625–5629.

Trudel et al., Biol. Abst. 85(1) Jan. 1, 1989, Abstract No. 4479.

Lambert, 1988, Virology, 164: 458–466.

Collins et al., 1986, Proc. Nat'l. Acad. Sci. USA. 81: 7683–7687.

Cohen et al., 1984, J. Virol. 49(1): 102–108.

Wagner et al. Bio. Abst. 82(9) Nov. 1, 1986 Abstract No. 82911.

Hildreth et al., 1986, Abstract ASM Annual Meeting p. 319, T-11.

Kim et al., 1971, Pediatrics, 48: 745.

Belshe et al., 1977, J. Med. Virol. 1: 157–162.

Richardson et al., 1978, J. Med. Virol. 3: 91–100.

Wright, et al., 1982, Infect. Immun. 37: 397–400.

Buynak et al., 1978, Proc. Soc. Exp. Biol. Med. 157: 636–642.

Prince et al., 1979, Infect. Immun. 26: 1009–1013.

Prince et al., 1985, J. Virol. 55: 517–520.

FIG. 1

Nucleotide and Amino Acid Sequences of the
Fusion Protein from the A2 Strain of RS Virus

|  |  |  |  |  |  |  |  |  |  |  |  | G | GGG | CAA | ATA | ACA | ATG | GAG | TTG | 22 |
|---|---|---|---|---|---|---|---|---|---|---|---|---|---|---|---|---|---|---|---|---|
|  |  |  |  |  |  |  |  |  |  |  |  |  |  |  |  |  | Met | Glu | Leu | 3 |
| CTA | ATC | CTC | AAA | GCA | AAT | GCA | AAT | ACC | ACA | ATC | CTC | ACT | GCA | GTC |  |  |  |  |  | 67 |
| Leu | Ile | Leu | Lys | Ala | Asn | Ala | Ile | Thr | Thr | Ile | Leu | Thr | Ala | Val |  |  |  |  |  | 18 |
| ACA | TTT | TGT | TTT | GCT | TCT | GGT | CAA | AAC | ATC | ACT | GAA | GAA | TTT | TAT |  |  |  |  |  | 112 |
| Thr | Phe | Cys | Phe | Ala | Ser | Gly | Gln | Asn | Ile | Thr | Glu | Glu | Phe | Tyr |  |  |  |  |  | 33 |
| CAA | TCA | ACA | TGC | AGT | GCA | GTT | AGC | AAA | GGC | TAT | CTT | AGT | GCT | CTG |  |  |  |  |  | 157 |
| Gln | Ser | Thr | Cys | Ser | Ala | Val | Ser | Lys | Gly | Tyr | Leu | Ser | Ala | Leu |  |  |  |  |  | 48 |
| AGA | ACT | GGT | TGG | TAT | ACC | AGT | GTT | ATA | ACT | ATA | GAA | TTA | AGT | AAT |  |  |  |  |  | 202 |
| Arg | Thr | Gly | Trp | Tyr | Thr | Ser | Val | Ile | Thr | Ile | Glu | Leu | Ser | Asn |  |  |  |  |  | 63 |
| ATC | AAG | GAA | AAT | AAG | TGT | AAT | GGA | ACA | GAT | GCT | AAG | GTA | AAA | TTG |  |  |  |  |  | 247 |
| Ile | Lys | Glu | Asn | Lys | Cys | Asn | Gly | Thr | Asp | Ala | Lys | Val | Lys | Leu |  |  |  |  |  | 78 |
| ATA | AAA | CAA | GAA | TTA | GAT | AAA | TAT | AAA | AAT | GCT | GTA | ACA | GAA | TTG |  |  |  |  |  | 292 |
| Ile | Lys | Gln | Glu | Leu | Asp | Lys | Tyr | Lys | Asn | Ala | Val | Thr | Glu | Leu |  |  |  |  |  | 93 |
| CAG | TTG | CTC | ATG | CAA | AGC | ACA | CCA | CCA | ACA | AAC | AAT | CGA | GCC | AGA |  |  |  |  |  | 337 |
| Gln | Leu | Leu | Met | Gln | Ser | Thr | Pro | Pro | Thr | Asn | Asn | Arg | Ala | Arg |  |  |  |  |  | 108 |
| AGA | GAA | CTA | CCA | AGG | TTT | ATG | AAT | TAT | ACA | CTC | AAC | AAT | GCC | AAA |  |  |  |  |  | 382 |
| Arg | Glu | Leu | Pro | Arg | Phe | Met | Asn | Tyr | Thr | Leu | Asn | Asn | Ala | Lys |  |  |  |  |  | 123 |
| AAA | ACC | AAT | GTA | ACA | TTA | AGC | AAG | AAA | AGG | AAA | AGA | AGA | TTT | CTT |  |  |  |  |  | 427 |
| Lys | Thr | Asn | Val | Thr | Leu | Ser | Lys | Lys | Arg | Lys | Arg | Arg | Phe | Leu |  |  |  |  |  | 138 |
| GGT | TTT | TTG | TTA | GGT | GTT | GGA | TCT | GCA | ATC | GCC | AGT | GGC | GTT | GCT |  |  |  |  |  | 472 |
| Gly | Phe | Leu | Leu | Gly | Val | Gly | Ser | Ala | Ile | Ala | Ser | Gly | Val | Ala |  |  |  |  |  | 153 |
| GTA | TCT | AAG | GTC | CTG | CAC | CTA | GAA | GGG | GAA | GTG | AAC | AAG | ATC | AAA |  |  |  |  |  | 517 |
| Val | Ser | Lys | Val | Leu | His | Leu | Glu | Gly | Glu | Val | Asn | Lys | Ile | Lys |  |  |  |  |  | 168 |
| AGT | GCT | CTA | CTA | TCC | ACA | AAC | AAG | GCT | GTA | GTC | AGC | TTA | TCA | AAT |  |  |  |  |  | 562 |
| Ser | Ala | Leu | Leu | Ser | Thr | Asn | Lys | Ala | Val | Val | Ser | Leu | Ser | Asn |  |  |  |  |  | 183 |
| GGA | GTT | AGT | GTC | TTA | ACC | AGC | AAA | GTG | TTA | GAC | CTC | AAA | AAC | TAT |  |  |  |  |  | 607 |
| Gly | Val | Ser | Val | Leu | Thr | Ser | Lys | Val | Leu | Asp | Leu | Lys | Asn | Tyr |  |  |  |  |  | 198 |
| ATA | GAT | AAA | CAA | TTG | TTA | CCT | ATT | GTG | AAC | AAG | CAA | AGC | TGC | AGC |  |  |  |  |  | 652 |
| Ile | Asp | Lys | Gln | Leu | Leu | Pro | Ile | Val | Asn | Lys | Gln | Ser | Cys | Ser |  |  |  |  |  | 213 |
| ATA | TCA | AAT | ATA | GAA | ACT | GTG | ATA | GAG | TTC | CAA | CAA | AAG | AAC | AAC |  |  |  |  |  | 697 |
| Ile | Ser | Asn | Ile | Glu | Thr | Val | Ile | Glu | Phe | Gln | Gln | Lys | Asn | Asn |  |  |  |  |  | 228 |
| AGA | CTA | CTA | GAG | ATT | ACC | AGG | GAA | TTT | AGT | GTT | AAT | GCA | GGT | GTA |  |  |  |  |  | 742 |
| Arg | Leu | Leu | Glu | Ile | Thr | Arg | Glu | Phe | Ser | Val | Asn | Ala | Gly | Val |  |  |  |  |  | 243 |
| ACT | ACA | CCT | GTA | AGC | ACT | TAC | ATG | TAA | ACT | AAT | AGT | GAA | TTA | TTG |  |  |  |  |  | 787 |
| Thr | Thr | Pro | Val | Ser | Thr | Tyr | Met | Leu | Thr | Asn | Ser | Glu | Leu | Leu |  |  |  |  |  | 258 |

```
TCA TTA ATC AAT GAT ATG CCT ATA ACA AAT GAT CAG AAA AAG TTA  832
Ser Leu Ile Asn Asp Met Pro Ile Thr Asn Asp Gln Lys Lys Leu  273

ATG TCC AAC AAT GTT CAA ATA GTT AGA CAG CAA AGT TAC TCT ATC  877
Met Ser Asn Asn Val Gln Ile Val Arg Gln Gln Ser Tyr Ser Ile  288

ATG TCC ATA ATA AAA GAG GAA GTC TTA GCA TAT GTA GTA CAA TTA  922
Met Ser Ile Ile Lys Glu Glu Val Leu Ala Tyr Val Val Gln Leu  303

CCA CTA TAT GGT GTT ATA GAT ACA CCC TGT TGG AAA CTA CAC ACA  967
Pro Leu Tyr Gly Val Ile Asp Thr Pro Cys Trp Lys Leu His Thr  318

TCC CCT CTA TGT ACA ACC AAC ACA AAA GAA GGG TCC AAC ATC TGT 1012
Ser Pro Leu Cys Thr Thr Asn Thr Lys Glu Gly Ser Asn Ile Cys  333

TTA ACA AGA ACT GAC AGA GGA TGG TAC TGT GAC AAT GCA GGA TCA 1057
Leu Thr Arg Thr Asp Arg Gly Trp Tyr Cys Asp Asn Ala Gly Ser  348

GTA TCT TTC TTC CCA CAA GCT GAA ACA TGT AAA GTT CAA TCA AAT 1102
Val Ser Phe Phe Pro Gln Ala Glu Thr Cys Lys Val Gln Ser Asn  363

CGA GTA TTT TGT GAC ACA ATG AAC AGT TTA ACA TTA CCA AGT GAA 1147
Arg Val Phe Cys Asp Thr Met Asn Ser Leu Thr Leu Pro Ser Glu  378

ATA AAT CTC TGC AAT GTT GAC ATA TTC AAC CCC AAA TAT GAT TGT 1192
Ile Asn Leu Cys Asn Val Asp Ile Phe Asn Pro Lys Tyr Asp Cys  393

AAA ATT ATG ACT TCA AAA ACA GAT GTA AGC AGC TCC GTT ATC ACA 1237
Lys Ile Met Thr Ser Lys Thr Asp Val Ser Ser Ser Val Ile Thr  408

TCT CTA GGA GCC ATT GTG TCA TGC TAT GGC AAA ACT AAA TGT ACA 1282
Ser Leu Gly Ala Ile Val Ser Cys Tyr Gly Lys Thr Lys Cys Thr  423

GCA TCC AAT AAA AAT CGT GGA ATC ATA AAG ACA TTT TCT AAC GGG 1327
Ala Ser Asn Lys Asn Arg Gly Ile Ile Lys Thr Phe Ser Asn Gly  438

TGC GAT TAT GTA TCA AAT AAA GGG ATG GAC ACT GTG TCT GTA GGT 1372
Cys Asp Tyr Val Ser Asn Lys Gly Met Asp Thr Val Ser Val Gly  453

AAC ACA TTA TAT TAT GTA AAT AAG CAA GAA GGT AAA AGT CTC TAT 1417
Asn Thr Leu Tyr Tyr Val Asn Lys Gln Glu Gly Lys Ser Leu Tyr  468

GTA AAA GGT GAA CCA ATA ATA AAT TTC TAT GAC CCA TTA GTA TTC 1462
Val Lys Gly Glu Pro Ile Ile Asn Phe Tyr Asp Pro Leu Val Phe  483

CCC TCT GAT GAA TTT GAT GCA TCA ATA TCT CAA GTC AAC GAG AAG 1507
Pro Ser Asp Glu Phe Asp Ala Ser Ile Ser Gln Val Asn Glu Lys  498

ATT AAC CAG AGC CTA GCA TTT ATT CGT AAA TCC GAT GAA TTA TTA 1552
Ile Asn Gln Ser Leu Ala Phe Ile Arg Lys Ser Asp Glu Leu Leu  513
```

FIGURE 1 con't

```
CAT AAT GTA AAT GCT GGT AAA TCC ACC ACA AAT ATC ATG ATA ACT  1597
His Asn Val Asn Ala Gly Lys Ser Thr Thr Asn Ile Met Ile Thr   528

ACT ATA ATT ATA GTG ATT ATA GTA ATA TTG TTA TCA TTA ATT GCT  1642
Thr Ile Ile Ile Val Ile Ile Val Ile Leu Leu Ser Leu Ile Ala   543

GTT GGA CTG CTC TTA TAC TGT AAG GCC AGA AGC ACA CCA GTC ACA  1687
Val Gly Leu Leu Leu Tyr Cys Lys Ala Arg Ser Thr Pro Val Thr   558

CTA AGC AAA GAT CAA CTG AGT GGT ATA AAT AAT ATT GCA TTT AGT  1732
Leu Ser Lys Asp Gln Leu Ser Gly Ile Asn Asn Ile Ala Phe Ser   573

AAC TAA ATA AAA ATA GCA CCT AAT CAT GTT CTT ACA ATG GTT TAC  1777
Asn ***                                                        574

TAT CTG CTC ATA GAC AAC CCA TCT GTC ATT GGA TTT TCT TAA AAT  1822

CTG AAC TTC ATC GAA ACT CTC ATC TAT AAA CCA TCT CAC TTA CAC  1867

TAT TTA AGT AGA TTC CTA GTT TAT AGT TAT AT                    1899
```

FIGURE 1 con't

LOCATION OF SYNTHETIC PEPTIDES FOR PEPTIDE MAPPING

| NAME | RESIDUES | SEQUENCE |
|------|----------|----------|
| SP1 | 136–169 | S-K-V-L-H-L-E-G-E-V-N-K-I-K-S |
| SP2 | 500–512 | N-Q-S-L-A-F-I-R-K-S-D-E-L |
| SP3 | 414–429 | V-S-C-Y-G-K-T-K-C-T-A-S-N-K-N-R |
| SP4 | 261–273 | I-N-D-M-P-I-T-N-D-Q-K-K-L |
| SP5 | 320–340 | P-L-C-T-T-N-T-L-E-G-S-N-I-C-L-T-R-T-D-R-G |

FIG.6

AMINO ACID SEQUENCE AT THE AMINO AND CARBOXYTERMINI
OF THE RECOMBINANT PROTEINS

A. AMINO TERMINI

| CONSTRUCTION | LAC z | POLYLINKER | FUSHION PROTEIN |
|---|---|---|---|
| F3 | NH₂-M-T-M-I-T- | P-S-L-H-S-C-W-S- | T-N-S.... |
| F4, F8, F7, F10 | NH₂-M-T-M-I-T- | P-S-L-H-S- | C-S-I.... |
| F11 | NH₂-M-T-M-I-T- | P-S-L-H-S- | Y-V-V.... |

B. CARBOXY TERMINI

| CONSTRUCTION | F | POLYLINKER | LAC z |
|---|---|---|---|
| F3 | ...-F-S-N-COOH | | |
| F4, F11 | ...-F-D-A- | G-R-L-COOH | |
| F8 | ...-C-N-V- | D-S-R-G-S-P-G-T-E- | L-E-F-T-G-R-R-K-T-T-S-COOH |
| F7 | ...-Q-S-N- | R-P-A-G-R-L-COOH | |
| F10 | ...-V-L-A-COOH | | |

DOT BOLT OF SYNTHETIC PEPTIDES WITH L4
MONOCLONAL ANTIBODY

RESPIRATORY SYNCYTIAL VIRUS: VACCINES

CROSS REFERENCE TO RELATED APPLICATION

This application is a continuation-in-part of application Ser. No. 07/102,180, filed Sep. 29, 1987, currently abandoned.

TABLE OF CONTENTS

1. Field of the Invention
2. Background of the Invention
   2.1 Respiratory Syncytial Virus in Disease
   2.2 Immunological Approach to the Prevention of RS Virus Infection
   2.3 Recombinant DNA Technology and Gene Expression
      2.3.1. *E. coli* As An Expression Vector
      2.3.2. Vaccinia Virus As An Expression Vector
      2.3.3. Baculovirus As An Expression Vector
3. Summary of the Invention
4. Brief description of the Figures
5. Detailed Description of the Invention
   5.1 Identification of a Neutralizing and/or Fusion Epitope[s] Of RS Virus Fusion Protein
      1.1.1 Mapping by Defined Proteolytic Cleavage
      5.1.2 Cloning and Expressing Fragments of the Fusion Protein
      5.1.3 Synthesis of Antigenic Peptides
   5.2 Preparation of Proteins, Polypeptides and Peptides Related to RS Virus Fusion Protein and G Protein
   5.3 Insertion of the RS Virus Fusion Protein or G Protein Coding Sequences into Expression Vectors
   5.4 Identification of Recombinant Expression Vectors Capable of Replicating and Expressing the Inserted Gene
   5.5 Identification and Purification of the Expressed Gene Product
   5.6 Determination of the Immunopotency of the Recombinant Product
   5.7 Formulation of a Vaccine
      5.7.1 Subunit Vaccine Formulations
      5.7.2 Viral Vaccine Formulations
      5.7.3 Passive Immunity and Anti-Idiotypic Antibodies
   5.8 Diagnostic Assays
      5.8.1 Immunoassays
      5.8.2 Nucleic Acid Hybridization Assay
6. Protection of Animals: RS Virus Fusion Protein
   6.1 General Procedures
      6.1.1 Isolation of Fusion Protein
      6.1.2 Assays
         6.1.2.1 Virus Neutralization Assay
         6.1.2.2 Anti-Fusion Assay
         6.1.2.3 Enzyme Immunoassay (EIA)
   6.2 Protection of Animals: Homologous and Heterologous Protection
   6.3 Protection of Baboons
   6.4. Protection Against Bovine RS Virus
   6.5. Avoidance of Enhanced Disease
7. Protection of Humans: RS Virus Fusion Protein
8. Identification of Neutralizing and/or Fusion Epitopes[s] of RS Virus Fusion Protein
   8.1 General Procedures
      8.1.1 Protein Immunoblot (Western Blot Analysis)
      8.1.2 Coupling of Peptides to Keyhole Lympet Hemocyanin (KLH) and Production of Rabbit Antisera
      8.1.3 Proteolytic Cleavage of Fusion Protein
      8.1.4 Dot Blot Analysis
   8.2 Mapping by Defined Proteolytic Cleavage
   8.3 Mapping by Expression of Protein Fragments
   8.4 Mapping by Synthetic Peptides
9. Immunogenicity of Modified RS Virus Fusion Protein
   9.1. Conformational Modification
   9.2. Deacylated Fusion Protein
10. Protection of Animals: RS Virus G Protein
    10.1. Isolation of G Protein
    10.2. Passive Protection
    10.3. Active Immunization and Protection
11. Immunogenicity of RS Virus G Protein Expressed in Recombinant Vectors
12. Cell-Mediated Immunological Aspects of RS Virus Vaccine
13. Deposit of Microorganisms

1. FIELD OF THE INVENTION

Respiratory Syncytial (RS) virus is a major cause of lower respiratory disease in infancy and early childhood. It is a matter of great medical and scientific interest to provide safe and effective vaccines against this virus.

RS virus is an enveloped RNA virus. The major outer envelope proteins, the F protein (also known as the fusion protein or fusion glycoprotein) and the G protein, play a key role in RS viral infection because antibodies directed against these proteins can neutralize the virus.

For the purposes of this Application, a neutralizing epitope on a viral protein is an epitope which is essential for virus infectivity as defined by the fact that antibody binding to the epitope neutralizes the virus. Likewise, a fusion epitope on a viral protein is an epitope which is essential for virus-cell fusion or intercellular spread of infection by fusion between an infected-cell and an uninfected cell as defined by the fact that antibody-binding to the epitope abrogates fusion.

The present invention relates to compositions and methods of preparation of proteins and polypeptides associated with the outer envelope of RS virus. More particularly, one embodiment of the invention is directed to compositions and methods for preparation of proteins and polypeptides related to the fusion protein of RS virus. The proteins and polypeptides of this embodiment of the invention are related to a neutralizing epitope, or a fusion epitope, or both, of the fusion protein, and may be used as immunogens in vaccine formulations including multivalent vaccines for active immunization and for the generation of antibodies for use in passive immunization, as well as reagents for diagnostic assays.

Another embodiment of the invention is directed to compositions and methods for preparation of proteins and polypeptides related to the G protein of RS virus. The proteins and polypeptides of this embodiment of the invention are related to a neutralizing epitope of the G protein, and may be used as immunogens in vaccine formulations including multivalent vaccines for active immunization and for the generation of antibodies for use in passive immunization, as well as reagents for diagnostic assays.

The novel proteins and polypeptides related to a neutralizing epitope, a fusion epitope, or both can be obtained by using either recombinant DNA or chemical synthetic methods. Additionally, the invention relates to novel DNA sequences and vectors useful for expressing RS virus related proteins and polypeptides and to cells which harbor the novel DNA sequences and vectors.

It should be noted that an epitope is a three dimensional structure generated by the molecular arrangement of an underlying molecular entity. In the present invention, the underlying molecular entities are polypeptides. It is well known that the structural properties of polypeptides of which three dimensional configuration is one, may only be minutely changed by the introduction of a small number of modifications such as substitutions, insertions and deletions of one or more amino acids. Generally, such substitutions in the amino acid sequence of a polypeptide are in the amount of less than twenty percent, more usually less than ten percent. Generally, conservative substitutions are less likely to make significant structural changes than non-conservative substitutions, which in turn are less likely to make significant structural changes than insertions or deletions. Examples of conservative substitutions are glycine for alanine; valine for isoleucine; aspartic acid for glutamic acid; asparagine for glutamine; serine for threonine; lysine for arginine; phenylalanine for threonine; and the converse of the above. Therefore, it is to be understood that the present invention embraces modified polypeptides so long as the epitope is unchanged.

It is also well known that viral epitopes may exhibit strain-to-strain variations. Adjustment by the above-indicated modifications may indeed be used advantageously.

Finally, the fusion protein and G protein related polypeptides or proteins of the invention, like the bonafide viral proteins, may be labeled or unlabeled, bound to a surface, conjugated to a carrier, and the like, depending on the use to which they are put.

BACKGROUND OF THE INVENTION

2.1. Respiratory Syncytial Virus in Disease

RS virus is a major cause of lower respiratory disease in infancy and early childhood (McIntosh and Chanock, 1985, in Virology, Fields, B. (ed), Raven, NY, pp. 1285–1304). In all geographical areas, it is the major cause of bronchiolitis and pneumonia in infants and young children. The agent reinfects frequently during childhood, but illness produced by reinfection is generally milder than that associated with the initial infection and rarely causes major problems.

RS virus is an enveloped RNA virus of the family Paramyxoviridae and of the genus pneumovirus. The two major envelope proteins are the G protein, which is responsible for attachment of the virus to the host cell membrane, and the fusion protein, which is responsible for fusing the virus and cell membranes. Virus-cell fusion is a necessary step for infection. Fusion protein is also required for cell-cell fusion which is another way to spread the infection from an infected cell to an uninfected cell.

Antibodies directed against the fusion protein or against the G protein can neutralize the virus. However, only antibodies to the fusion protein will block the spread of the virus between cells, i.e. have anti-fusion activity. Thus, antibodies to the fusion protein will protect against circulating virus as well as inhibit the spread, between cells, of an established infection. Antibodies to the fusion protein (both polyclonal antisera against purified fusion protein and monoclonal antibodies which contain both neutralizing and anti-fusion activity) have been found to be protective in animal models against infection (Walsh et al., 1984, Infect. Immun. 43:756–758).

2.2. Immunological Approach to the Prevention of Virus Infection

A practical means for protection of infants and young children against upper and lower respiratory disease would be protective vaccination against RS virus. Vaccination of expectant mothers (active immunization) would protect young children by passive transfer of immunity, either transplacentally, or through the mother's milk. Several approaches to an RS virus vaccine are possible, but some of them have proven unsuccessful in the past.

Vaccination with killed RS virus vaccine has been tried and found to be ineffective (Kim et al., 1969, Am. J. Epid. 89:422). Not only were children not protected, but in some cases, subsequent infections with RS virus resulted in atypical and more severe disease than in the unimmunized controls. This phenomenon is not unique to RS virus and has been seen also in killed paramyxovirus vaccines such as measles. It has been suggested that the reason for the failure of the past inactivated RS virus vaccine was due to inactivation of the biologically functional epitopes on either or both of the viral envelope glycoproteins. That is to say, the neutralizing and fusion epitopes on the killed virus vaccine were "denatured". As a result, the vaccinated subject did not experience the biologically functional neutralizing and fusion epitopes. Therefore, when the vaccinated subject encountered a live virus, the resultant antibody response did not yield protective immunity. Instead, there was an antibody mediated inflammatory response which often resulted in a more severe disease (Choppin and Scheid, 1980, Rev. Inf. Dis., 2:40–61).

The second approach to an RS virus vaccine has been to attenuate live virus. Temperature sensitive mutants (Wright et al., 1982, Infect. Immun. 37:397–400) and passage attenuated virus (Belshe et al., 1982, J. Inf. Dis. 145:311–319) have proven to be poorly infectious and not efficacious in the prevention of disease when used as immunogens in RS virus vaccines. However, in these cases, there was no atypical disease as a result of vaccination.

Based on our current knowledge of the structure of RS virus and the immune response to infection, it is clear that a useful vaccine to this virus must be effective in inducing production of antibodies to the fusion protein and/or the G protein. Of particular importance to protective immunity is the production of antibodies that inhibit fusion and therefore, can stop the spread of virus between cells in the respiratory tract. Additionally, it may be helpful to induce a cell mediated immune response, including the stimulation of cytotoxic T cells (CTL's) which are useful against RS virus infected cells. The various vaccine formulations of the present invention are directed to meeting both these objectives.

2.3. Recombinant DNA Technology and Gene Expression

Recombinant DNA technology involves insertion of specific DNA sequences into a DNA vehicle (vector) to form a recombinant DNA molecule which is capable of being replicated in a host cell. Generally, but not necessarily, the inserted DNA sequence is foreign to the recipient DNA vehicle, i.e., the inserted DNA sequence and DNA vector are derived from organisms which do not exchange genetic information which in nature, or the inserted DNA sequence comprises information which may be wholly or partially artificial. Several general methods have been developed which enable construction of recombinant DNA molecules. For example, U.S. Pat. No. 4,237,224 to Cohen and Boyer describes production of such recombinant plasmids using processes of cleavage of DNA with restriction enzymes and joining the DNA pieces by known methods of ligation.

These recombinant plasmids are then introduced by means of transformation and replicated in unicellular cultures including procaryotic organisms and eucaryotic cells grown in tissue culture. Because of the general applicability of the techniques described therein, U.S. Pat. No. 4,237,224 is hereby incorporated by reference into the present specification. Another method for introducing recombinant DNA molecules into unicellular organisms is described by Collins and Hohn in U.S. Pat. No. 4,304,863 which is also incorporated herein by reference. This method utilizes a packaging, transduction system with bacteriophage vectors (cosmids).

DNA sequences may also be inserted into viruses, for example, vaccinia virus. Such recombinant viruses may be generated, for example, by transfection of plasmids into cells infected with virus (Chakrabarti et al., 1985, Mol. Cell. Biol. 5:3403-3409).

Regardless of the method used for construction, the recombinant DNA molecule is preferably compatible with the host cell, i.e., capable of being replicated in the host cell either as part of the host chromosomes or as an extra-chromosomal element. The recombinant DNA molecule or recombinant virus preferably has a marker function which allows the selection of the desired recombinant DNA molecule(s) or virus(es). In addition, if all of the proper replication, transcription and translation signals are correctly arranged on the recombinant DNA molecule, the foreign gene will be properly expressed in the transformed or transfected host cells.

Different genetic signals and processing events control gene expression at different levels. For instance, DNA transcription is one level, and messenger RNA (mRNA) translation is another. Transcription of DNA is dependent upon the presence of a promoter which is a DNA sequence that directs the binding of RNA polymerase and thereby promotes RNA synthesis. The DNA sequences of eucaryotic promoters differ from those of procaryotic promoters. Furthermore, eucaryotic promoters and accompanying genetic signals may not be recognized in or may not function in a procaryotic system.

Similarly, translation of mRNA in procaryotes depends upon the presence of the proper procaryotic signals which differ from those of eucaryotes. Efficient translation of mRNA in procaryotes requires a ribosome binding site called the Shine-Dalgarno (SD) sequence on the mRNA. For a review on maximizing gene expression, see Roberts and Lauer, 1979, Methods in Enzymology 68:473.

Many other factors complicate the expression of foreign genes in procaryotes even after the proper signals are inserted and appropriately positioned. One such factor is the presence of an active proteolytic system in *E. coli* and other bacteria. This protein-degrading system appears to destroy foreign proteins selectively. A tremendous utility, therefore, would be afforded by the development of a means to protect eucaryotic proteins expressed in bacteria from proteolytic degradation. One strategy is to construct hybrid genes in which the foreign sequence is ligated in phase (i.e., in the correct reading frame) with a procaryotic structural gene. Expression of this hybrid gene results in a recombinant protein product (a protein that is a hybrid of procaryotic and foreign amino acid sequences).

Similar considerations of gene expression in eukaryotic systems have been discussed in Enhancers & Eukaryotic Gene Expression, Gluzman & Shenk (Eds.), Cold Spring Harbor Laboratories, Cold Spring Harbor, New York 1983, and Eukaryotic Viral Vectors, Gluzman (Ed.), Cold Spring Harbor Laboratories, Cold Spring Harbor, N.Y. 1982.

Successful expression of a cloned gene requires efficient transcription of DNA, translation of the mRNA and in some instances post-translational modification of the protein. Expression vectors have been developed to increase protein production from the cloned gene. In expression vectors, the cloned gene is often placed next to a strong promoter which is controllable so that transcription can be turned on when necessary. Cells can be grown to a high density and then the promoter can be induced to increase the number of transcripts. These, if efficiently translated will result in high yields of protein. This is an especially valuable system if the foreign protein is deleterious to the host cell.

Several recombinant DNA expression systems are described below for the purpose of illustration only, and these examples should not be construed to limit the scope of the present invention.

2.3.1. *E. Coli* As an Expression Vector

Many *E. coli* plasmids are known and have been used to express foreign genes. For economic reasons, it would be highly preferable to be able to obtain a high level of expression. One way to obtain large amounts of a given gene product is to clone a gene on a plasmid which has a very high copy number within the bacterial cell. By increasing the number of copies of a particular gene, mRNA levels would normally also increase, which in turn would lead to increased production of the desired protein.

2.3.2. Vaccinia Virus as an Expression Vector

Vaccinia virus may be used as a cloning and expression vector. The virus contains a linear double-stranded DNA genome of approximately 187 kb pairs and replicates within the cytoplasm of infected cells. These viruses contain a complete transcriptional enzyme system (including capping, methylating and polyadenylating enzymes) within the virus core. This system is necessary for virus infectivity because vaccinia virus transcriptional regulatory sequences (promoters) allow for initiation of transcription by vaccinia RNA polymerase, but not by cellular RNA polymerase.

Expression of foreign DNA in recombinant viruses requires the fusion of vaccinia promoters to protein coding sequences of the foreign gene. Plasmid vectors, also called insertion vectors have been constructed to insert the chimeric gene into vaccinia virus. One type of insertion vector comprises: (1) a vaccinia virus promoter including the transcriptional initiation site; (2) several unique restriction endonuclease cloning sites downstream from the transcriptional start site for insertion of foreign DNA fragments; (3) nonessential vaccinia virus DNA (such as the thymidine kinase gene) flanking the promoter and cloning sites which direct insertion of the chimeric gene into the homologous nonessential region of the virus genome; and (4) a bacterial origin of replication and antibiotic resistance marker for replication and selection in *E. coli*. Examples of such vectors are described by MacKett (1984, J. Virol. 49:857–864).

Recombinant viruses are produced by transfection of recombinant bacterial insertion vectors containing the foreign gene into cells infected with vaccinia virus. Homologous recombination takes place within the infected cells and results in the insertion of the foreign gene into the viral genome. Immunological techniques, DNA plaque hybridization, or genetic selection can be used to identify and isolate the desired recombinant virus. These vaccinia recombinants retain the functions essential for infectivity and can be constructed to accommodate up to approximately 35 kb of foreign DNA.

Expression of a foreign gene can be detected by enzymatic or immunological assays (e.g., immunoprecipitation, enzyme-linked immunosorbent assay (ELISA), radio-immunoassay, or immunoblotting). Additionally, naturally occurring membrane glycoproteins produced from recombinant vaccinia infected cells are glycosylated and may be transported to the cell surface. High expression levels can be obtained by using strong promoters or cloning multiple copies of a single gene.

2.3.3. Baculovirus as an Expression Vector

A baculovirus, such as *Autographica californica* nuclear polyhedris virus (AcNPV) has also been used as a cloning or expression vector. The infectious form of AcNPV is normally found in a viral occlusion. This structure is largely composed of polyhedrin polypeptide in which virus particles are embedded. Polyhederin gene expression occurs very late in the infection cycle, after mature virus particles are formed. Therefore, polyhedrin gene expression is a dispensable function, i.e., non-occluded virus particles produced in the absence of polyhedrin gene expression are fully active and are capable of infecting cells in culture. According to European Patent Application Serial No. 84105841.5 by Smith et al., a recombinant baculovirus expression vector can be prepared in two steps. First, baculovirus DNA is cleaved to produce a fragment comprising a polyhedrin gene or a portion thereof, which fragment is inserted into a cloning vehicle. The gene to be expressed is also inserted into the cloning vehicle; and it is so inserted that it is under control of the polyhedrin gene promoter. This recombinant molecule is called a recombinant transfer vector. Normally, the recombinant transfer vector in amplified in appropriate host cells. Second, the recombinant transfer vector formed in this way is mixed with baculovirus helper DNA and used to transfect insect cells in culture to effect recombination and incorporation of the cloned gene at the polyhedrin gene locus of the baculovirus genome. The resultant recombinant baculovirus is used to infect susceptible insects or cultured insect cells.

3. SUMMARY OF THE INVENTION

The present invention is directed to polypeptides and proteins related to a neutralizing epitope, a fusion epitope, or both, of respiratory syncytial (RS) virus glycoproteins, including the fusion protein and G protein, as well as molecularly cloned gene or gene fragments encoding such polypeptides and proteins.

One embodiment of the present invention is directed to polypeptides and proteins related to a neutralizing epitope, a fusion epitope, or both, of the fusion protein of respiratory RS virus as well as molecularly cloned genes or gene fragments, which encode these polypeptides or proteins. Another embodiment of the present invention is directed to polypeptides and proteins related to a neutralizing epitope of the G protein of RS virus as well as molecularly cloned genes or gene fragments, which encode these polypeptides or proteins. The polypeptides or proteins of the present invention may be used as immunogens in subunit vaccine formulations for RS virus or as reagents in diagnostic immunoassays for RS virus. The polypeptides or proteins of the present invention may be produced using recombinant DNA techniques or synthesized by chemical methods.

The present invention is also directed to methods for the molecular cloning of and expression of genes or gene fragments encoding a neutralizing or a fusion epitope, or both, of RS virus fusion protein or a neutralizing epitope of the G protein. Accordingly, the invention is also directed to the construction of novel polynucleotide sequences and their insertion into vectors, including both RNA and DNA vectors, to form recombinant molecules or viruses which can be used to direct expression of polypeptides or proteins related to the epitope(s) in the appropriate host cells. The vectors include plasmid DNA, viral DNA, human viruses, animal viruses, insect viruses and bacterial phages.

Recombinant viruses or extracts of cells which comprise the polypeptides or proteins of the present invention can also be used as immunogens in viral vaccine formulations. Since a fusion or neutralizing epitope of a virus will be recognized as "foreign" in the host animal, humoral and cell mediated immune responses directed against the epitope(s) will be induced. In a properly prepared vaccine formulation, this should protect the host against subsequent RS virus infection.

The polypeptides and proteins of the present invention can also be used as reagents in immunoassays such as ELISA tests and radioimmunoassays to detect RS virus infections in blood samples, body fluids, tissues, and so forth.

The polynucleotide sequences of the present invention can also be used as reagents in nucleic acid hybridization assays to detect RS virus in blood samples, body fluids, tissues, and so forth.

4. BRIEF DESCRIPTION OF THE FIGURES

FIG. 1 shows the complete nucleotide and amino acid sequences of the RS virus fusion protein, reproduced from Collins et al., 1985, Proc. Nat'l Acad. Sci. USA, 81:7683–7687.

FIG. 2 shows the electrophoretic behavior in SDS-polyacrylamide gel of 1 ug of the purified RS virus fusion protein under various conditions. In lane 2, the protein was reduced with 5% beta-mercaptoethanol and heated to 100° C. prior to electrophoresis; in lane 3, the protein was heated to 100° C. prior to electrophoresis; in lane 4, the protein was not heated or reduced prior to electrophoresis. Lane 1 contains standard marker proteins whose molecular weights are indicated in the left margin. The right margin shows the molecular weight of the various fusion protein components. The gel was stained with silver for visualization.

FIG. 3 shows the positions of synthetic polypeptides 1, 2, 3, 4, and 5 (sp1–sp5) ) on a linear map of the $F_1$ subunit. The $F_1$ subunit encompasses amino acids 137–574. FIG. 3 also shows the exact amino acid sequence of the synthetic polypeptides.

FIG. 6 shows the amino and carboxy terminal sequences of several recombinant proteins expressed in *E. coli*.

Figure 8:
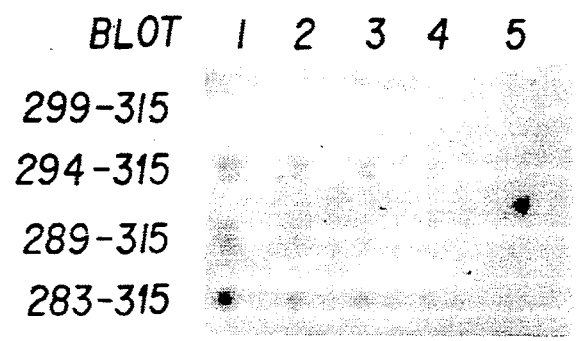

FIG. 8 illustrates a dot blot autoradiogram of the four (4) synthetic polypeptides defined by the chains of amino acids shown in the left margin. Lanes 1–4 contain 20 ug, 15 ug, 10 ug and 5 ug of peptide respectively. Lane 5 contains a positive fusion protein control. The blot was reacted with the L4 monoclonal antibody and then with $^{125}$I-protein A.

Figure 9:
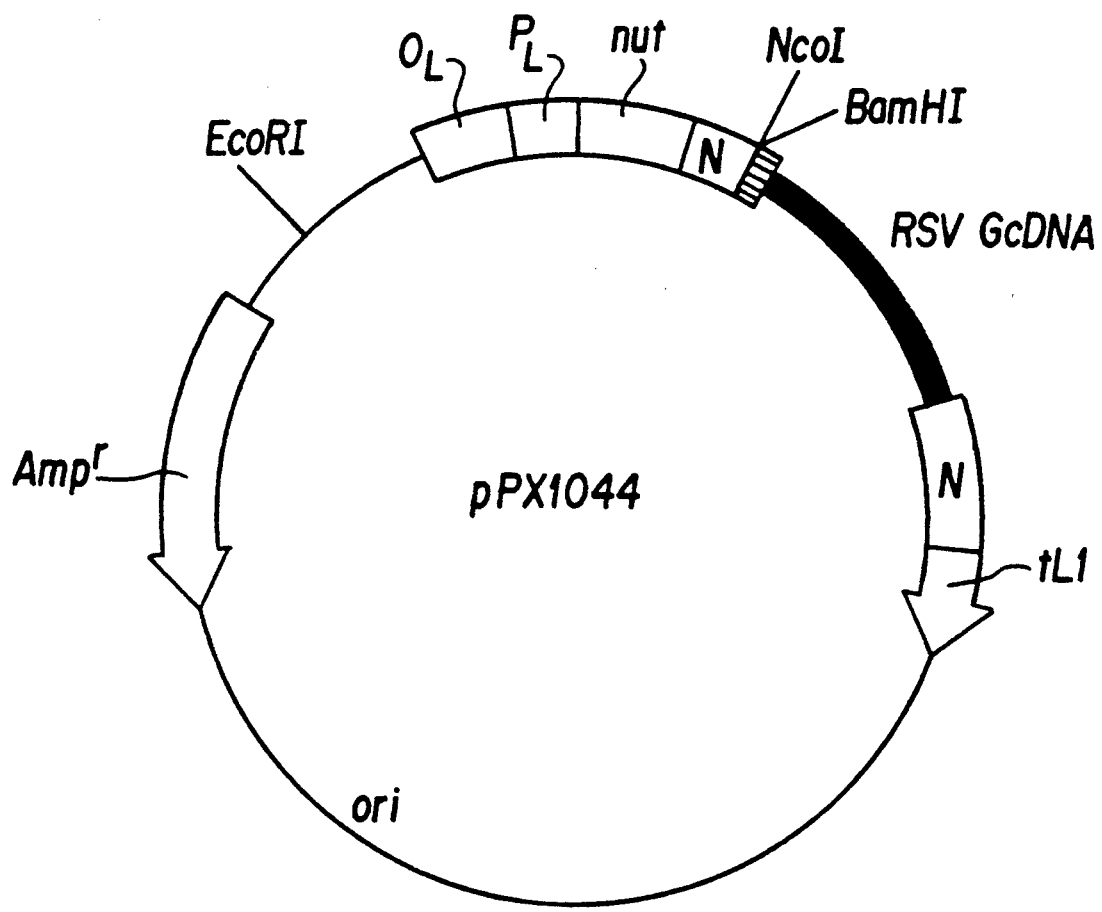

FIG. 9 is a diagramatic representation of a recombinant expression vector of pPX1044 containing the complete nucleotide sequence of the RS virus G protein gene.

DETAILED DESCRIPTION OF THE INVENTION

According to one embodiment of the present invention, a region of the RS virus fusion protein which defines a neutralizing and fusion epitope[s] has been identified. A method for producing novel proteins, polypeptides and peptides comprising the epitope[s], and the polynucleotide sequences which encode such novel protein and polypeptides are provided.

The fusion protein of RS virus has an apparent molecular weight of 70,000 daltons by sodium dodecyl sulphate polyacrylamide gel electrophoresis (SDS-PAGE). The primary (cistronic) translation product consisting of 574 amino acid residues is synthesized and subsequently processed by enzymatic cleavage at a trypsin sensitive site yielding two subunits designated $F_1$ (amino acids 137–574) and $F_2$ (amino acids 1–136).

The complete nucleotide sequence of the fusion protein gene from the A2 strain of RS virus (Collins et al., 1984, Proc. Nat'l Acad. Sci. USA, 81:7683–7687) which encodes the fusion protein of 574 amino acids is illustrated in FIG. 1. The numbering system depicted in FIG. 1 is used throughout this application. The $F_1$ (apparent molecular weight 48,000 dalton) and $F_2$ (apparent molecular weight 23,000 dalton) subunits are linked through a disulfide bond to form a protein which is designated $F_{1,2}$ (apparent molecular weight about 70,000 daltons). When purified from RS virus or infected cells, the native fusion protein exists predominantly as a dimer (apparent molecular weight 140,000 daltons). The dimeric form is the most immunogenic form of the RS virus fusion protein.

Figure 2:
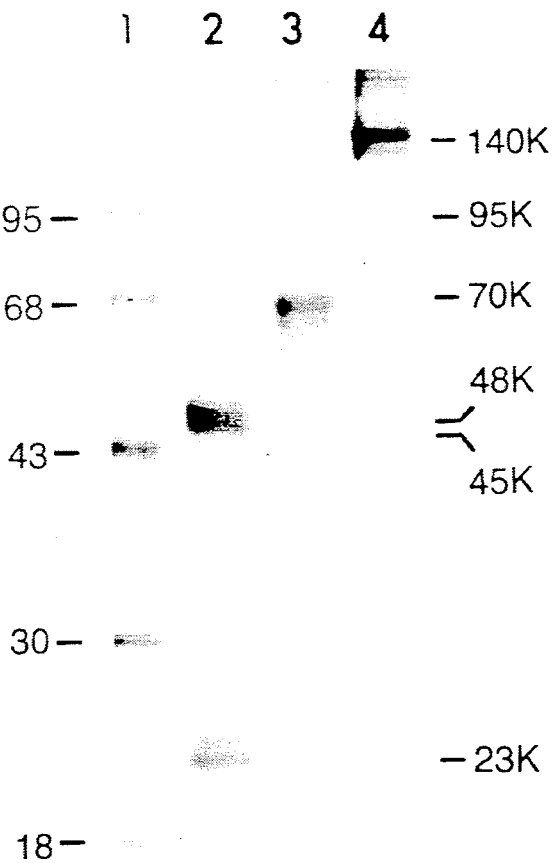

FIG. 2 shows the electrophoretic mobility of various fusion protein components using SDS-PAGE. In lane 2, the protein was reduced with 5% beta-mercaptoethanol and heated to 100° C. prior to electrophoresis; in lane 3, the protein was heated to 100° C. prior to electrophoresis; in lane 4, the protein was not heated or reduced prior to electrophoresis. Lane I contains standard marker proteins whose molecular weights are indicated in the left margin. The right margin shows the molecular weight of the various fusion protein components. The gel was stained with silver for visualization (Morrissey, 1981, Anal. Biochem. 117:307–310).

Active immunization of cotton rats with purified RS virus fusion protein (the 140,000 dalton form) results in the production of antibodies which are effective in virus neutralization and in preventing fusion (see, for example, Section 6.2, infra). As demonstrated in Section 6.2, this immunization protected the lung and nasal tissues from infection by RS virus. Similar results have been obtained in baboons (see, Section 6.3, infra). Additionally, active immunization of animals with purified RS virus fusion protein previously reduced with beta-mercaptoethanol protects animals from subsequent RS virus infection (see Section 6.2, infra).

According to another embodiment of the present invention, substantially pure polypeptides and proteins related to a neutralizing epitope of the RS virus G protein are provided. The RS virus G protein has an apparent molecular weight of about 84,000–90,000 daltons and is highly glycosylated. The nucleotide sequence of the gene encoding the RS virus G protein has been disclosed (Satake et al., 1985, Nucleic Acid Res. 13:7795–812; Wertz et al., 1985, Proc. Nat'l Acad. Sci. USA 82:4075–79. The entire gene sequence encoding the RS G protein has been cloned and expressed in a recombinant expression vector (see Section 9, infra). Surprisingly, active immunization of animals with a recombinant non-glycosylated RS virus G protein induced a protective immune response (see Section 10, infra).

A monoclonal antibody to the fusion protein, designated L4 (Walsh and Hruska, 1983, J. Virol. 47:171–177), is capable of both neutralizing RS virus and inhibiting fusion. Therefore, it appears that this antibody reacts with an epitope on the fusion protein which is essential to both infectivity and the fusion function of the fusion protein, i.e., this antibody reacts with both a fusion epitope and a neutralizing epitope. Moreover, passive transfer of the L4 monoclonal antibody will protect cotton rats from virus infection in their lungs (Walsh et al., 1984, Infect. Immun., 43:756–758).

In addition to the L4 type antifusion, neutralizing epitope, there is yet another antifusion, neutralizing epitope of the fusion protein which may be conformationally dependent. This epitope is recognized by monoclonal antibody A5 (Walsh et al., 1986, J. Gen. Virol. 67:505–513). The reactivity of this antibody appears to be dependent upon the native conformation of the fusion protein. When the conformation of the fusion protein is altered either by heat treatment or by heat treatment and the reduction of disulfide bonds, the A5 type epitope is destroyed. The present studies have examined the role of L4 type and A5 type epitopes of the RS virus fusion protein on the formulation of the protein as an effective vaccine. Results from a competitive ELISA indicate that one third of the fusion protein specific antibody in human adults recovering from natural RS infection, is directed against epitopes recognized by either L4 or A5. Vaccination with purified F protein produces a response which can be 80% blocked by a combination of L4 and A5. Competitive binding to the F protein, shows that these epitopes overlap by 40%. Based on these studies, it appears that the functional antifusion, neutralizing epitopes can be classified into two categories, L4 type and A5 type.

5.1. Identification of Neutralizing and/or Fusion Epitope[S] of Virus Fusion Protein According to the present invention, the region of the RS virus fusion protein which is an epitope responsible for eliciting both neutralizing and antifusion antibodies has now been determined. This region has been defined by three methods. The first method employs defined proteolytic cleavage of the native protein. The second method relates to cloning and expressing fragments of the fusion protein gene, for example, in *E. coli*. The third relates to synthesis of synthetic polypeptides which bind to neutralizing and antifusion antibodies. In all three methods reactivity with the L4 monoclonal antibody was used to identify desired fragments. Any other monoclonal antibody which is capable of neutralizing and preventing fusion of RS virus may be used.

5.1.1. Mapping by Defined Proteolytic Cleavage

The L4 monoclonal antibody was tested for its ability to bind to the fusion protein subunits ($F_1$ and $F_2$) by protein immunoblot (Western blot) analysis. Using Western blot as described in Section 8.1, infra, the L4 monoclonal antibody was able to bind only to the $F_1$ subunit. Additionally, the L4 monoclonal antibody has been shown to bind to serotype B virus (Anderson et al., 1985, J. Inf. Dis 151:623-33) defined by the prototype virus designated strain 18537.

In order to map the $F_1$ subunit, synthetic polypeptides are prepared which correspond to various regions along the $F_1$ subunit. These synthetic polypeptides are coupled to a carrier protein, such as keyhole lympet hemocyanin (KLH), and then used separately to immunize rabbits (see Section 8, infra). In the particular example exemplified in Section 8.2., five antisera (anti-sp1 through anti-sp5) were obtained. Each antiserum produced in the rabbits reacted with the uncoupled synthetic polypeptide corresponding to the immunogen which induced the antiserum, i.e., anti-sp1 reacted with sp1; anti-sp2 reacted with sp2, etc. All five antisera reacted with the $F_1$ subunit of the fusion protein.

The purified fusion protein is then subjected to proteolytic cleavage under a variety of conditions (see Section 8, infra). In the example illustrated in Section 8.2, infra, the proteases used were (1) trypsin which specifically cleaves after lysine and arginine residues, (2) endoproteinase Arg-C which cleaves specifically after arginine residues, and (3) endoproteinase Lys-C which cleaves specifically after lysine residues. Cleavage after a residue means the breaking of a peptide bond at the carboxyl end of the residue. It should be understood that other combinations of proteases can be used. Therefore, the presently exemplified combination should not be construed as a limitation on the present invention.

Cleavages are also performed in the presence and absence of the L4 monoclonal antibody. The cleaved protein fragments are separated by SDS-PAGE and the cleavage products analyzed by Western blot analysis for the ability to bind to the L4 monoclonal antibody as well as the anti-synthetic polypeptide antibodies (See an exemplary illustration Section 8.2, infra). The positions of the proteolytic fragments within the fusion protein sequence are deduced from the reactivities of these cleavage fragments with each of the anti-synthetic polypeptide antisera. For example, as illustrated in Section 8.2., a cleavage fragment generated by trypsin digestion which fragment reacted with anti-sp1 would be expected to comprise amino acids 155-169. Furthermore, the fragment must have arginine or lysine at its carboxyl end and a N-terminal residue which follows a lysine or arginine in the sequence of FIG. 1. Finally, the molecular weight of a fragment can be determined by its mobility in SDS-PAGE. This set of information uniquely predicts that the 28,000 dalton fragment generated by trypsin digestion and reactive with anti-sp1 spans amino acids 137-394 of the $F_1$ polypeptide. The positions of the other cleavage fragments are similarly deduced.

The relationship between the positions of the cleavage fragments and the reactivities of these fragments to the L4 monoclonal antibody are analyzed. From the example presented in Section 8.2., it can readily be seen that amino acids 283-327 define the region which is common to all of the L4 positive fragments and absent from all of the L4 negative fragments. This region, therefore, comprises a virus neutralizing and/or antifusion epitope of the RS virus defined by the L4 monoclonal antibody.

5.1.2. Cloning and Expressing Fragments of the Fusion Protein

The cDNA illustrated in FIG. 1 containing the complete nucleotide sequence of the fusion protein gene is cloned into a cloning vector such as the *E. coli* plasmid vector pBR322. Due to the degeneracy of the nucleotide coding sequences, other DNA sequences which encode substantially the same amino acid sequence as depicted in FIG. 1 may be used. These include but are not limited to nucleotide sequences comprising all or portions of the fusion protein nucleotide sequences depicted in FIG. 1 which are altered by the substitution of different codons that encode the same or a functionally equivalent amino acid residue within the sequence (for example, an amino acid of the same polarity) thus producing a silent change.

Regions of the fusion protein gene are excised from the cloning vector by restriction endonuclease digestion and ligated into a compatible expression vector (see infra). In the experimental example described in Section 8.2., infra, the *E. coli* expression vector pUC19 (Yanish-Perron et al., 1985, Gene 33:103-19) was used. The expressed recombinant proteins are screened for reactivity first with polyclonal rabbit antiserum to native fusion protein to identify recombinant fragments and then with L4 monoclonal to identify those fragments comprising the neutralizing and antifusion epitope. As illustrated in Section 8.3., the RS virus fusion protein sequence common to all of the recombinant proteins reactive with the L4 monoclonal antibody is defined by amino acid residues 253-298.

5.1.3. Synthesis of Antigenic Peptides

In order to confirm the identify of the neutralizing and antifusion epitope identified as described above, synthetic polypeptides can be prepared corresponding in particular to amino acid residues 299-315; 294-315; 289-315; and 283-315 of the RS virus fusion protein. These peptides are analyzed for reactivity with L4 monoclonal antibody. As illustrated in Section 8.4., infra, polypeptides containing residues 294-315; 289-315; and 283-315 react positively with L4; whereas peptide 299-315 does not. This indicates that a neutralizing and fusion epitope resides between residues 283-298 and may be as small as residues 294-299.

5.2. Preparation of Proteins, Polypeptides and Peptides Related to RS Virus Fusion Protein and G Protein The proteins, polypeptides and peptides of the present invention can be prepared in a wide variety of ways. The polypeptides, because of their relatively short size may be synthetized in solution or on a solid support in accordance with conventional techniques. Various automatic synthesizers are commercially available and can be used in accordance with known protocols. See, for example, Stewart and Young, 1984, Solid Phase Peptide Synthesis, 2d Ed., Pierce Chemical Co. The structural properties of polypeptides, of which three dimensional configuration is one, may only be minutely changed by the introduction of a small number of modifications such as substitutions, insertions and deletions of one or more amino acids. Generally, such substitutions in the amino acid sequence of a polypeptide are in the amount of less than twenty percent, more usually less than ten percent. Generally, conservative substitutions are less likely to make significant structural changes than non-conservative substitutions, which in turn are less likely to make significant structural changes than insertions or deletions. Examples of conservative substitutions are glycine for alanine; valine for isoleucine; aspartic acid for glutamic acid; asparagine for glutamine; serine for threonine; lysine for arginine; phenylalanine for threonine; and the converse of the above. Therefore, it is to be understood that the present invention embraces modified polypeptides so long as the epitope of the RS virus fusion protein remains unchanged.

It is also well known that viral epitopes may exhibit strain-to-strain variations. Adjustment by the above-indicated modifications may indeed be used advantageously.

The polypeptides of the present invention may be employed as labeled or unlabeled compounds depending on their use. By label is intended a moiety which provides, directly or indirectly, a detectable signal. Various labels may be employed, such as radionuclides, enzymes, fluorescers, chemiluminescers, enzyme substrates, cofactors or inhibitors, particles (e.g. magnetic particles), ligands (e.g. biotin) and receptors (e.g. avidin) or the like. In addition, the polypeptides may be modified in a variety of ways for binding to a surface e.g. microtiter plate, glass beads, chromatographic surface, e.g. paper, cellulose and the like. The particular manner in which the polypeptides are joined to another compound or surface is conventional and finds ample illustration in the literature. See, for example, U.S. Pat. Nos. 4,371,515; 4,487,715 and the patents cited therein.

Alternatively, recombinant DNA technology may be employed to prepare the polypeptides biosynthetically.

5.3. Insertion of the RS Virus Fusion Protein or G Protein Coding Sequences into Expression Vectors The nucleotide sequence coding for the RS virus fusion protein or a portion thereof or for the RS virus G protein or a portion thereof is inserted into an appropriate expression vector, i.e. a vector which contains the necessary elements for the transcription and translation of the inserted protein-coding sequence. According to a preferred embodiment of this mode of the invention, nucleotide sequences coding for a neutralizing and/or fusion epitope of the fusion protein is inserted into an appropriate expression vector. The coding sequence may be extended at either the 5' and 3' terminus or both termini to extend biosynthetically the polypeptide while retaining the epitope. The extension may provied an arm for linking, e.g., to a label (see below), to a carrier or surface. The extension may provide for immunogenicity which may other wise be lacking in some of the shorter antigenic polypeptides of the invention.

A variety of host-vector systems may be utilized to express the protein-coding sequence. These include but are not limited to mammalian cell cultures such as Chinese hamster ovary cell host cultures, etc.; mammalian cell systems infected with virus (e.g. vaccinia virus, adenovirus, etc.); insect cell systems infected with virus (e.g. baculovirus); microorganisms such as yeast containing yeast vectors or bacteria transformed with bacteriophage DNA, plasmid DNA or cosmid DNA. In one embodiment the expression vector can be an attenuated enteroinvasive bacteria including but not limited to Salmonella spp., enteroinvasive E. coli (EIEC), and Shigella spp. Such bacterium can invade gut epithelial tissue, disseminate throughout the reticuloendothalical system and gain access to mesenteric lymphoid tissue where they multiply and induce humoral and cell-mediated immunity. The expression elements of these vectors vary in their strength and specificities. Depending on the host-vector system utilized, any one of a number of suitable transcription and translation elements may be used. For instance, when cloning in mammalian cell systems, promoters isolated from the genome of mammalian cells, (e.g., mouse metallothionien promoter) or from viruses that grow in these cells, (e.g. vaccinia virus 7.5K promoter) may be used. Promoters produced by recombinant DNA or synthetic techniques may also be used to provide for transcription of the inserted sequences.

Specific initiation signals are also required for efficient translation of inserted protein coding sequences. These signals include the ATG initiation codon and adjacent sequences. In cases where the RS virus fusion protein gene or the RS virus G protein gene including its own initiation codon and adjacent sequences are inserted into the appropriate expression vectors, no additional translational control signals may be needed. However, in cases where only a portion of the RS virus fusion protein or G protein coding sequence is inserted, exogenous translational control signals, including the ATG initiation codon must be provided. The initiation codon must furthermore be in phase with the reading frame of the protein coding sequences to ensure translation of the entire insert. These exogenous translational control signals and initiation codons can be a variety of origins, both natural and synthetic.

Any of the methods previously described for the insertion of DNA fragments into a vector may be used to construct expression vectors containing a chimeric gene consisting of appropriate transcriptional/translational control signals and the protein coding sequences. These methods may include in vitro recombinant DNA and synthetic techniques and in vivo recombinations (genetic recombination).

The invention is not limited to the use of E. coli or procaryotic expression vectors. Expression vectors which can be used include, but are not limited to the following vectors or their derivatives: human or animal viruses such as vaccinia viruses or adenoviruses; insect viruses such as baculoviruses; yeast vectors; bacteriophage vectors, and plasmid and cosmid DNA vectors to name but a few.

In cases where an adenovirus is used as an expression vector, the RS virus fusion protein gene or fragment thereof or the RS virus G protein gene or fragment thereof is ligated to an adenovirus transcriptional/translational control complex, e.g., the late promoter and tripartite leader sequences. This chimeric gene is then inserted in the adenovirus genome by in vitro or in vivo recombination. Insertion in a non-essential region of the viral genome (e.g., region E1 or E3) will result in a recombinant virus that is viable and capable of expressing the RS virus fusion protein or G protein related protein in infected hosts. Presently, there are two strains of adenovirus (types 4 and 7) approved and used as vaccines for military personnel. They are prime candidates for use as vectors to express the RS virus fusion protein or G protein gene and fragments thereof.

In addition, a host cell strain may be chosen which modulates the expression of the inserted sequences, or modifies and processes the chimeric gene product in the specific fashion desired. Expression from certain promoters can be elevated in the presence of certain inducers, (e.g., zinc and cadmium ions for metallothionein promoters). Therefore, expression of the genetically engineered RS virus fusion protein or G protein or fragment thereof may be controlled. This is important if the protein product of the cloned foreign gene is lethal to host cells. Furthermore, modifications (e.g., glycosylation) and processing (e.g., cleavage) of protein products are important for the function of the protein. Different host cells have characteristic and specific mechanisms for the post-translational processing and modification of proteins. Appropriate cell lines or host systems can be chosen to ensure the correct modification an processing of the foreign protein expressed.

5.4. Identification of Recombinant Expression Vectors Capable of Replicating and Expressing the Inserted Gene Expression vectors containing foreign gene inserts can be identified by three general approaches: (a) DNA-DNA hybridization, b) presence or absence of "marker" gene functions, and (c) expression of inserted sequences. In the first approach, the presence of a foreign gene inserted in an expression vector can be detected by DNA-DNA hybridization using probes comprising sequences that are homologous to the foreign inserted gene. In the second approach, the recombinant vector/host system can be identified and selected based upon the presence or absence of certain "marker" gene functions (e.g., thymidine kinase activity, resistance to antibiotics, transformation phenotype, occlusion body formation in baculovirus etc.) caused by the insertion of foreign genes in the vector. For example, if the RSV virus fusion protein gene or fragment thereof is inserted within the marker gene sequence of the vector, recombinants containing the RS virus fusion protein inserted can be identified by the absence of the marker gene function. In the third approach, recombinant expression vectors can be identified by assaying the foreign gene product expressed by the recombinant. Such assays can be based on the physical, immunological, or functional properties of the gene product.

Once a particular recombinant DNA molecule is identified and isolated, several methods may be used to propagate it, depending on whether such a recombinant constitutes a self-replicating unit (a replicon). A self replicating unit, e.g., plasmids, viruses, cells etc., can multiply itself in the appropriate cellular environment and growth conditions. Recombinants lacking a self-replicating unit will have to be integrated into a molecule having such a unit in order to be propagated. For example, certain plasmid expression vectors upon introduction into a host cell need to be integrated into the cellular chromosome to ensure propagation and stable expression of the recombinant gene. Once a suitable host system and growth conditions are established, recombinant expression vectors can be propagated and prepared in quantity.

5.5. Identification and Purification of the Expressed Gene Product

Once a recombinant which expresses the RS virus fusion protein gene or fragment thereof or the RS virus G protein or fragment thereof is identified, the gene product should be analyzed. This can be achieved by assays based on the physical, immunological or functional properties of the product. Immunological analysis is especially important where the ultimate goal is to use the gene products or recombinant viruses that express such products in vaccine formulations and/or as antigens in diagnostic immunoassays.

A variety of antisera are available for analyzing imunoreactivity of the product, including but not limited to L4 monoclonal antibody, A5 monoclonal antibody, polyclonal antisera raised against purified fusion protein or G protein as described in Section 6 or 9, infra.

The protein should be immunoreactive whether it results from the expression of the entire gene sequence, a portion of the gene sequence or from two or more gene sequences which are ligated to direct the production of chimeric proteins. This reactivity may be demonstrated by standard immunological techniques, such as radioimmunoprecipitation, radioimmune competition, or immunoblots.

Once the RS virus fusion or G protein related protein is identified, it may be isolated and purified by standard methods including chromatography (e.g., ion exchange, affinity, and sizing column chromatography), centrifugation, differential solubility, or by any other standard technique for the purification of proteins.

5.6. Determination of the Immunopotency of the Recombinant Product

Immunopotency of the RS virus fusion or G protein related product can be determined by monitoring the immune response of test animals following immunization with the purified protein, synthetic peptide or protein. In cases where the RS virus fusion protein or G protein related protein is expressed by an infectious recombinant virus, the recombinant virus itself can be used to immunize test animals. Test animals may include but are not limited to mice, rats, rabbits, primates, and eventually human subjects. Methods of introduction of the immunogen may include oral, intradermal, intramuscular, intraperitoneal, intravenous, subcutaneous, intranasal or any other standard routes of immunizations. The immune response of the test subjects can be analysed by three approaches: (a) the reactivity of the resultant immune serum to authentic RS viral antigens, as assayed by known techniques, e.g., enzyme linked immunosorbant assay (ELISA), immunoblots, radioimmunoprecipitations, etc., (b) the ability of the immune serum to neutralize RS virus infectivity in vitro (see Section 6, infra), (c) the ability of the immune serum to inhibit virus fusion in vitro (see Section 6, infra) and (d) protection from RS virus infection (see Section 6, infra).

5.7. Formulation of a Vaccine

Many methods may be used to administer the vaccine formulations described herein to an animal or a human. These include, but are not limited to: oral, intradermal, intramuscular, intraperitoneal, intravenous, subcutaneous and intranasal routes. The secretory IgA antibodies produced by the mucosal associated lymphoid issue may play a major role in protection against RS virus infection by preventing the initial interaction of the pathogens with the mucosal surface, or by neutralizing the important epitopes of the pathogens that are involved in infection/or spreading of the disease. Stimulation of mucosal immune responses, including production of secretory IgA antibodies may be of major importance in conferring protection against lower and upper respiratory tract infection. When a live recombinant virus vaccine formulation is used, it may be administered via the natural route of infection of the parent wild-type virus which was used to make the recombinant virus in the vaccine formulation.

5.7.1. Subunit Vaccine Formulations

The proteins and polypeptides of the present invention related to a neutralizing and/or fusion epitope of the fusion protein of RS virus are useful as immunogens in a subunit vaccine to protect against lower respiratory disease and other disease symptoms of RS virus infection. Subunit vaccines comprise solely the relevant immunogenic material necessary to immunize a host. Vaccines prepared from genetically engineered immunogens, chemically synthesized immunogens and/or immunogens comprising authentic substantially pure RS virus fusion protein or fragments thereof alone or in combination with similarly prepared RS virus G protein or fragments thereof, which are capable of eliciting a protective immune response are particularly advantageous because there is no risk of infection of the recipients.

Thus, the RS virus fusion protein and/or G protein related proteins and polypeptides can be purified from recombinants that express the neutralizing and/or fusion epitopes. Such recombinants include any of the previously described bacterial transformants, yeast transformants, cultured cells infected with recombinant viruses or cultured mammalian cells such as Chinese hamster ovary cells that express the RS virus fusion protein epitopes (see Section 5.3, supra). Additionally the recombinants include recombinant attenuated enterovasive bacteria containing a DNA sequence which encodes a neutralizing and/or fusion epitope of Respiratory Syncytial Virus fusion protein or a neutralizing epitope of Respiratory Syncytial Virus G protein. Such recombinants are prepared using methods similar to those described in U.S. patent application Ser. No. 104,735. These recombinant attenuated enteroinvasive bacteria are particularly suited for oral vaccine formulations. The recombinant protein or poypeptides can comprise multiple copies of the epitope of interest.

Alternatively, the RS virus fusion protein and/or G protein related protein or polypeptide can be chemically synthesized (see Section 5.2, supra). In yet another alternative embodiment, the RS virus fusion protein related protein or polypeptide or G related protein can be isolated in substantially pure form from RS virus or cultures of cells infected with RS virus (see, for example, Section 6.1, or Section 10, infra).

Regardless of the method of production, the RS virus fusion protein or G protein, related protein or polypeptide is adjusted to an appropriate concentration and can be formulated with any suitable vaccine adjuvant. The polypeptides and proteins may generally be formulated at concentrations in the range of 0.1 ug to 100 ug per kg/host. Physiologically acceptable media may be used as carriers. These include, but are not limited to: sterile water, saline, phosphate buffered saline and the like. Suitable adjuvants include, but are not limited to: surface active substances, e.g., hexadecylamine, octadecylamine, octadecyl amino acid esters, lysolecithin, dimethyldioctadecylammonium bromide, N,N-dioctadecyl-N,-N-bis(2-hydroxyethyl-propane diamine), methoxyhexadecyglycerol, and pluronic polyols; polyamines, e.g., pyran, dextransulfate, poly IC, polyacrylic acid, carbopol; peptides, e.g., muramyl dipeptide, dimethylglycine, tuftsin; oil emulsions; and mineral gels, e.g., aluminum hydroxide, aluminum phosphate, etc. The immunogen may also be incorporated into liposomes or conjugated to polysaccharides and/or other polymers for use in a vaccine formulation.

In yet another embodiment of this mode of the invention, the RS virus fusion protein related protein or polypeptide is a hapten, i.e., a molecule which is antigenic in that it reacts specifically or selectively with cognate antibodies, but is not immunogenic in that it cannot elicit an immune response. In such case, the hapten may be covalently bound to a carrier or immunogenic molecule; for example, a large protein such as protein serum albumin will confer immunogenicity to the hapten coupled to it. The hapten-carrier may be formulated for use as a subunit vaccine.

The polypeptides and proteins of the present invention may be used when linked to a soluble macromolecular carrier. Preferably, the carrier and the polypeptides and proteins of the present invention are in excess of five thousand daltons after linking. More preferably, the carrier is in excess of five kilodaltons. Preferably, the carrier is a polyamino acid, either natural or synthetic, which is immunogenic in animals, including humans. The manner of linking is conventional. Many linking techniques are disclosed in U.S. Pat. No. 4,629,783 which is incorporated herein by reference. Many cross-linking agents are disclosed in 1986–87 Handbook And General Catalog, Pierce Chemical Company, (Rockford, Ill.) pages 311 to 340.

In yet another embodiment of this mode of the invention the immunogen of the vaccine formulation comprises a mixture of polypeptides and proteins related to the RS virus fusion protein and the G protein of one or more virus subtypes.

5.7.2. Viral Vaccine Formulations

Another purpose of the present invention is to provide either a live recombinant viral vaccine or an inactivated recombinant viral vaccine which is used to protect against lower respiratory infections and other disease symptoms of RS virus. To this end, recombinant viruses are prepared that express RS virus fusion protein related epitopes (see Section 5.2, supra). Where the recombinant virus is infectious to the host to be immunized but does not cause disease, a live vaccine is preferred because multiplication in the host leads to a prolonged stimulus, therefore, conferring substantially long-lasting immunity. The infectious recombinant virus when introduced into a host can express the RS virus fusion protein related protein or polypeptide fragment from its chimeric gene and thereby elicit an immune response against RS virus antigens. In cases where such an immune response is protective against subsequent RS virus infection, the live recombinant virus, itself, may be used in a preventative vaccine against RS virus infection. Production of such recombinant virus may involve both in vitro (e.g., tissue culture cells) and in vivo (e.g.. natural host animal) systems. For instance, conventional methods for preparation and formulation of smallpox vaccine may be adapted for the formulation of live recombinant virus vaccine expressing an RS virus fusion protein related protein or polypeptide.

Multivalent live virus vaccines can be prepared from a single or a few infectious recombinant viruses that express epitopes of organisms that cause disease in addition to the epitopes of RS virus fusion protein. For example, a vaccinia virus can be engineered to contain coding sequences for other epitopes in addition to those of RS virus fusion protein. Such a recombinant virus itself can be used as the immunogen in a multivalent vaccine. Alternatively, a mixture of vaccinia or other viruses, each expressing a different gene encoding for an epitope of RS virus fusion protein and an epitope of another disease causing organism can be formulated in a multivalent vaccine.

Whether or not the recombinant virus is infectious to the host to be immunized, an inactivated virus vaccine formulation may be prepared. Inactivated vaccines are "dead" in the sense that their infectivity has been destroyed, usually by chemical treatment (e.g., formaldehyde). Ideally, the infectivity of the virus is destroyed without affecting the proteins which are related to immunogenicity of the virus. In order to prepare inactivated vaccines, large quantities of the recombinant virus expressing the RS virus fusion protein related protein or polypeptide must be grown in culture to provide the necessary quantity of relevant antigens. A mixture of inactivated viruses which express different epitopes may be used for the formulation of "multivalent" vaccines. In certain instances, these "multivalent" inactivated vaccines may be preferable to live vaccine formulation because of potential difficulties with mutual interference of live viruses administered together. In either case, the inactivated recombinant virus or mixture of viruses should be formulated in a suitable adjuvant in order to enhance the immunological response to the antigens. Suitable adjuvants include, but are not limited to: surface active substances, e.g., hexadecylamine, octadecyl amino acid esters, octadecylamine, lysolecithin, dimethyl-dioctadecylammonium bromide, N,N-dicoctadecyl-N'-N-bis (2-hydroxyethyl-propane diamine), methoxyhexadecylglycerol, and pluronic polyols; polyamines, e.g., pyran, dextransulfate, poly IC, polyacrylic acid, carbopol; peptides, e.g., muramyl dipeptide, dimethylglycine, tuftsin; oil emulsions; and mineral gels, e.g., aluminum hydroxide, aluminum phosphate, etc.

5.7.3. Passive Immunity and Anti-Idiotypic Antibodies

Instead of actively immunizing with viral or subunit vaccines, it is possible to confer short-term protection to a host by the administration of pre-formed antibody against an epitope of RS virus fusion protein or an epitope of the RS virus G protein. Thus, the vaccine formulations can be used to produce antibodies for use in passive immunotherapy. Human immunoglobulin is preferred in human medicine because a heterologous immunoglobulin may provoke an immune response to its foreign immunogenic components. Such passive immunization could be used on an emergency basis for immediate protection of unimmunized individuals exposed to special risks, e.g., young children exposed to contact with RS virus patients. Alternatively, these antibodies can be used in the production of anti-idiotypic antibody, which is turn can be used as an antigen to stimulate an immune response against RS virus fusion protein or G protein epitopes.

5.8. Diagnostic Assays

Yet another purpose of the present invention is to provide reagents for use in diagnostic assays for the detection of antigens of the RS virus fusion protein or G protein (and hence RS virus) or for the detection of antibodies to the RS virus fusion protein or G protein in various body fluids of individuals suspected of RS virus infection.

5.8.1. Immunoassays

In one mode of this embodiment, the RS virus fusion protein or G protein related proteins, polypeptides and peptides of the present invention may be used as antigens in immunoassays for the detection of RS virus in various patient tissues and body fluids including, but not limited to: blood, spinal fluid, sputum, nasal secretions, secretions of the respiratory tract, etc.

The proteins, polypeptides and peptides of the present invention may be used in any immunoassay system known in the art including, but not limited to: radioimmunoassays, ELISA assay, "sandwich" assays, precipitin reactions, gel diffusion immunodiffusion assays, agglutination assays, fluoresent immunoassays, protein A immunoassays and immunoelectrophoresis assays, to name but a few. U.S. Pat. No. 4,629,783 and patents cited therein also describe suitable assays.

5.8.2. Nucleic Acid Hybridization Assay

In another mode of this embodiment, the novel nucleotide sequence of the gene or gene fragment encoding the RS virus fusion protein related proteins polypeptides and peptides of the present invention may be used as probes in nucleic acid hybridization assays for the detection of RS virus in various patient body fluids, including but not limited to: blood, sputum, nasal secretions, secretions of the respiratory tract, etc.

The nucleotide sequences of the present invention may be used in any nucleic acid hybridization assay system known in the art including, but not limited to: Southern blots (Southern, 1975, J. Mol. Biol. 98:508); Northern blots (Thomas et al., 1980, Proc. Nat'l Acad. Sci. USA 77:5201-05); colony blots (Grunstein et al., 1975, Proc. Nat'l Acad. Sci. USA 72:3961-65), etc.

The following Examples are offered for the purpose of illustrating the present invention and are not to be construed to limit the scope of the present invention.

6. Protection of Animals: RS Virus Fusion Protein

6.1. General Procedures

6.1.1. Isolation of Fusion Protein

Substantially pure RS virus fusion protein suitable for use as an immunogen in a subunit vaccine formulation was prepared essentially according to the procedure of Walsh et al. (1985, J. Gen. Virol. 66: 409-15). The procedure may be summarized as follows: Cells were infected with an RSV strain. The cells were lysed in a non-denaturing detergent buffer containing 1% Triton X-100 and deoxycholate. The cell lysates were clarified by centrifugation. Protein was purified from the cell lysates by immunoaffinity purification. A monoclonal antibody against the protein was coupled to beads and a column was constructed with those beads. RSV-infected cell lysates were applied to the column, and the column was washed with PBS containing 0.1% Triton X-100. Protein bound to the column was eluted with 0.1M glycine, pH 2.5, 0.1% Triton X-100. Elution samples were buffered with Tris and analyzed for the presence of protein. Fractions containing the protein were pooled and dialyzed against PBS. Rabbit polyclonal antiserum (previously obtained from rabbits immunized with the RSV fusion protein) and a monoclonal antibody, both specific for the RSV fusion protein, were used to verify the identity of the purified dimeric RSV fusion protein by Western blotting. Purified protein has been prepared from three different virus strains including Long, A2 and 18537 and from two different cell lines, HEp-2 (ATCC No. CCL23) and Vero (ATCC No. CCL81). The protein derived from all sources is highly immunogenic and when used as an immunogen produces antibody which is virus neutralizing and antifusing. The electrophoretic behavior of the purified protein derived from the Long strain of virus in HEp-2 cells can be seen in FIG. 2 under a variety of denaturing conditions. The protein is substantially pure of contaminating viral or cellular proteins.

The fusion glycoprotein purified as described above was found to have lipid covalently associated with the $F_1$ subunit. This was demonstrated by infecting Vero cells with the A2 strain of RS virus and labeling the cultures with $[9,10-^3H]$-palmitic acid. The purified protein as demonstrated to have $^3H$-palmitic acid associated with the 140,000 dalton dimeric form of the protein based on PAGE and autoradiography. Furthermore, treatment of the fusion protein with heat alone or with heat plus reduction of disulfide bonds showed that the $^3H$-palmitic acid was associated with the 70,000 and 48,000 dalton ($F_1$ subunit) forms of the protein.

When $^3H$-palmitic acid labeled protein was extracted with chloroform:methanol (2:1 v/v), nearly all of the label remained associated with the protein and was not extracted as free lipid into the chloroform:methanol. Therefore, the palmitic acid is covalently attached. When the protein was first treated with 1 M hydoxylamine at pH 7.0, the palmitic acid was then extracted into chloroform:methanol. Thus the protein-lipid bond is broken by hydroxylamine showing a covalent ester linkage. Since the bond was broken at neutral pH, a thioester linkage through cysteine on the protein is the most likely bond although other ester bonds could be formed.

In addition, preliminary experiments suggest that myristic acid is also present in the RS virus F Protein. Purified F protein was hydrolysed in 1M methanolic HCl at 80° C. for 24 hours; released lipid was extracted in hexane and analyzed by gas chromatography (GC) (Perkin Elmer 8500) using a fused silica column bonded with methyl silicone. The GC spectra obtained indicated the presence of mysristic acid on the purified F protein.

The carbohydrate nature of the purified fusion protein obtained as described above was also characterized. The purified protein derived from the Long strain of RS virus obtained from infected HEp-2 cells was analyzed as follows: The purified protein was methanolyzed with HCl-containing methanol, fully acetylated, O-deacylated, and finally per-O-(trimethylsilyl)ated. The sugar residues were identified and quantitated by gas liquid chromatorgraphy (Reinhold, 1972, Methods in Enzymology, 25:244–49). The protein was found to have 5.75% total carbohydrate by weight. The sugar composition by percentage of total sugar was: 11.5% fucose, 3.3% xylose, 26.2% mannose, 9.8% galactose, 9.8% glucose, and 39.3% N-acetyl-glucosamine.

6.1.2. Assays

6.1.2.1. Virus Neutralization Assay

Virus neutralization assays were performed as follows:

Test serum samples and the positive control serum were heat inactivated at 56° C. for 30 min. Test samples were serially diluted. All sera were then diluted with an equal volume containing about 50 plague forming units (PFU) of RS virus, and incubated at 37° C. for one hour. A pool of adult sera which had previously been characterized by enzyme immunoassay, neutralization and antifusion assays was used for positive control. Sera which had previously been characterized and was known to be non-immune was used as negative control.

Each incubated serum-virus mixture was inoculated to HEp-2 cells (ATCC No. CCL23) in a separate well of 24 well plates and virus adsorption was allowed to take place for 2 hours at 37° C. The inocula were removed. The cell monolayers were washed and overlayed with modified Eagle's medium plus 5% fetal bovine serum and 1% Sephadex ®, and incubated at 37° C. for 3 days. The overlay medium was removed and the cells were washed with phosphate buffered saline (PBS).

One ml of chilled PBS-methanol (1:5) solution was added to each well, and the cells were fixed for 30 min. at room temperature. The PBS-methanol fixative was removed, and one ml per well of 5% Carnation ™ instant milk in PBS, pH 6.8 (BLOTTO) was added. The plate was incubated for 30 minutes at 37° C.

The BLOTTO was removed. One-half ml per well of monoclonal antibodies against RS virus (previously titered and diluted with BLOTTO to a working concentration) was added, and the plate was incubated at 37° C. for 1 hour. The antibodies were removed, and the fixed cells were washed twice with BLOTTO, 30 minutes each time.

One-half ml/well of horseradish peroxidase conjugated goat anti-mouse IgG (diluted 1:250 in BLOTTO) was added and the plate was incubated for 1 hour at 37° C. The goat antibodies were removed, and the fixed cells were again washed twice with BLOTTO, 30 minutes each time.

One-half ml/well of a peroxidase substrate solution (0.05% 4 chloro-1-napthol, 0.09% $H_2O_2$ in PBS pH, 6.8) was added, and color was allowed to develop for 15-30 minutes at room temperature. The substrate solution was removed, and the wells were washed with water and air dried. The number of plaques in each well was determined.

The neutralization ability of a test serum sample is expressed as the dilution which results in a 60% reduction in plaque formation when compared to non-immune control serum expressed per ml of serum.

6.1.2.2. Anti-Fusion Assay

Anti-fusion assays were performed as follows:

HEp-2 cells in 48 well plates were infected with RS virus at 25 PFU/well for 6 hours at 37° C. After infection, the culture medium was replaced with fresh culture medium containing 0.1% K6 monoclonal antibodies (sterile filtered ascites fluid) and either a heat-inactivated test serum sample or a heat-inactivated non-immune control serum. K6 monoclonal antibody is specific for G glycoprotein of RS virus. The presence of K6 in the culture medium prevents virus spread via the culture medium. Sephadex ® was added to a final concentration of 1% and the plate incubated for 3 days at 37° C. The culture medium was removed and the cells were washed with PBS.

One ml of chilled PBS-methanol (1:5) solution was added to each well, and the cells were fixed for 30 min. at room temperature. The fixative was removed, and one ml per well of BLOTTO was added. The plate was incubated for 30 minutes at 37° C.

The BLOTTO was removed. One-half ml/well of monoclonal antibodies against RS virus (previously titered and diluted with BLOTTO to a working concentration) was added, and the plate was incubated for 1 hr. at 37° C. The antibody solution was removed and the fixed cells were washed twice with BLOTTO, 30 minutes each time.

One-half ml per well of horseradish peroxidase conjugated goat anti-mouse IgG diluted 1:250 in BLOTTO was added, and the plate was incubated for 1 hour at 37° C. The goat antibodies were removed, and the fixed cells were again washed twice with BLOTTO, 30 minutes each time.

One-half ml per well of a peroxidase substrate solution (PBS pH 6.8 containing 0.05% 4 chloro-1-napthol, 0.09% of $H_2O_2$) was added, and color was allowed to develop for 15-30 minutes at room temperature. The substrate solution was removed, and the wells were washed with water and air dried.

The number and typical size of plaques in the well corresponding to the non-immune control serum sample were determined. The number of plaques of a similar size was then determined for the wells corresponding to the test serum samples. The anti-fusion titer of a test serum sample is expressed as the dilution which yields a 60% reduction in plaques scored when compared to non-immune control serum expressed per ml of serum.

6.1.2.3. Enzyme Immunoassay (EIA)

Antibody titer in serum samples was determined using an Enzyme Immunoassay (EIA) performed as follows:

RS virus fusion protein was diluted to 200 ng/ml in carbonate-bicarbonate buffer, pH 9.6. One hundred ul of the diluted antigen was added to each well of rows B-G of a flat-bottomed, 96 well Nunc TM assay plate. In rows A and H, 100 ul of carbonate-bicarbonate buffer alone was added to each well. The plate was covered and incubated for 2 hours at 37° C. with shaking and then stored overnight at 4° C. to immobilize the antigen.

The supernatants were removed from the Nunc TM assay plate and the plate was washed with 0.1% Tween/PBS pH 7.4 and pat dried.

Three antibody samples were assayed on each plate. Each sample was first diluted to a primary dilution in 0.2% Tween, 0.01 M EDTA/PBS pH 7.5 (0.2% TWN). The primary dilutions were further serially diluted as follows in a 96 well U-bottomed Falcon TM plate:

(a) The primary dilutions of the samples were inoculated into row 2 at 200 ul/well. Sample 1 was inoculated in triplicate, =.g., in wells A2, B2, and C2; Sample 2 in duplicate e.g., in wells D2, E2; Sample 3 in triplicate e.g. in wells F2, G2, and H2.

(b) 100 ul of 0.2% TWN were inoculated into each well of rows 3-12.

(c) Serial dilutions were created by transferring sequentially 100 ul from a well in row 2 to the corresponding well in row 3 (e.g. B2 to B3; C2 to C3), a well in row 3 to the corresponding well in row 4, until row 12 was reached.

(d) To row 1, 100 ul of 0.2% TWN was added to each well as control.

One hundred ul of the primary dilutions were transferred from each well of the Falcon TM plate to the corresponding well in the Nunc TM plate, e.g., A2 (Falcon TM) to A2 (Nunc TM). The Nunc TM assay plate was covered and incubated for 1 hour at 37° C. with shaking. The supernatants were removed from the assay plate, and the plate was washed with 0.1% Tween/PBS and pat dried.

Goat anti-Mouse IgG alkaline phosphatase conjugate (TAGO TM) was diluted with 0.3% Tween/PBS pH 7.0 (0.3% TWN) to a working dilution, e.g., 1:1500. The diluted conjugate (100 ul) was added to each well in rows 2-12. To row 1, 100 ul of 0.3% TWN were added to each well as control. The plate was covered and incubated for 1 hour at 37° C. with shaking. The inocula was then removed, and the plate was washed with 0.1% Tween/PBS pH 7.4 and pat dried.

To each and every well, 100 ul substrate solution, 1 mg/ml in diethanolamine buffer pH 9.8 (SIGMA-104 TM) were added. The enzymatic reaction was allowed to take place at room temperature for 1 hour. The reaction was then stopped by adding 100 ul of 3N NaOH to each well. The extent of enzymatic reaction was determined by reading the optical density at 410 nm.

Rows A and H served as negative controls because no antigen was present; row 1 was also served as a negative control because no antibodies were present.

6.2. Protection of Animals: Homologous and Heterologous Protection

In one experiment, eighteen cotton rats were divided into 6 groups of 3 animals each. At week 0, 2 and 4-5, animals were actively immunized by intramuscular injection of 10 ug RS virus fusion protein (140,000 daltons), except Group 6 which received only 5 ug protein, in different adjuvants: Group 1, PBS; Group 2, IFA; Group 3, ISCOM; and Group 4, alum. Group 5 received intramuscular injections of PBS alone and served as the control group. Group 6 received intramuscular injections of RS virus fusion protein previously reduced using beta-mercaptoethanol, but without any adjuvant.

Serology assays were performed as described in Section 6.1.2, supra on serum samples obtained at week 6-7. Results are presented in Table 1.

Animals were challenged between weeks 6-7 with $1 \times 10^4$ PFU RS virus. Lungs were harvested on day 4 post-challenge. The presence and/or quantity of RS virus in lung tissues was determined. At day 4 post-infection, the lung and nasal turbinates were removed from the animals and homogenized in 1-2 ml of virus transport media (MEM, 5% FBS, 2 mM glutamine, 20 mM HEPES, 10% SPG). After centrifugation, the supernatants were serially diluted and applied to HEp-2 cells in 24 well tissue culture plates and the virus grown.

Plaques were identified as described in Section 6.1.2.1. (Virus Neutralization Assay) and expressed per gram of tissue. Results are also presented in Table 1.

TABLE 1

IMMUNOGENICITY OF RSV FUSION PROTEIN IN COTTON RATS

| Group No. (Adjuvant)[a] | Serology[b] | | | Protection[c] | |
|---|---|---|---|---|---|
| | EIA | Virus Neutralization | Anti-fusion | Virus Present | Titer |
| Group 1 (PBS) | 6.2 | 4.4 | 2.0 | 0 | 0 |
| Group 2 (IFA) | 7.3 | 5.1 | 2.9 | 0 | 0 |
| Group 3 (ISCOM) | 7.4 | 4.5 | 2.6 | 0 | 0 |
| Group 4 (ALUM) | 7.1 | 5.2 | 2.7 | 0 | 0 |
| Group 5 (control) | <1.0 | <2.0 | <1.0 | 3 | 4.8 |
| Group 6 (none) | 4.9 | 2.3 | 2.4 | 3 | 1.1 |

[a]Group 6 received fusion protein treated with beta mercaptoethanol and no adjuvant.
[b]Assays were performed on samples from week 7. Results represent the geometric mean titer three animals expressed in $\log_{10}$ units. See text for experimental details.
[c]Three animals in each of Groups 1-5 and 4 animals in Group 6 were challenged at weeks 6-7 and lungs were harvested on day 4 post-challenge. Virus was isolated from the lung tissues. "Virus present" represents the number of animals in each group in which virus was detectable. "Titer" represents the geometric mean titer (PFU/gm of tissue) of virus isolated from lung tissue.

As demonstrated in Table 1, immunization with RS virus fusion protein elicited production of antibodies effective virus neutralization and in preventing fusion. Moreover, results illustrated in Table 1 clearly demonstrate that lung tissues of immunized animals are effectively protected against subsequent RS virus infection.

When the fusion protein is treated (reduced) with betamercaptoethanol, the subunits are dissociated yielding free $F_1$ and $F_2$. When cotton rats were immunized with 5 ug of the reduced protein without adjuvant, they also produced antibody that was neutralizing and had antifusion activity (see Table 1, Group 6), although the level of these activities was reduced. Similarly, the lungs of these animals were substantially protected from infection, however, with less efficacy. Thus, the subunits of the fusion glycoprotein, presented in a dissociated form to the immune system, are able to produce protective immunity. It should also be noted that under these conditions, the $F_1$ subunit, which contains the hydrophobic membrane anchor region, will aggregate forming higher molecular weight multimers which may enhance immunity.

Human RS virus is subdivided into two subtypes, A and B. The fusion proteins from both subtypes share antigenic determinants and these determinants are highly conserved among RS virus strains. Hence a series of experiments were conducted to determine whether immunization with F protein from one subtype of human RS virus would confer protection against infection by both subtypes of human RS virus.

In this series of experiments, 30 cotton rats were divided into 4 groups of experimental animals and 4 groups of control animals. At week 0, 2 and 4, experimental animals were actively immunized by intramuscular injection of 10 ug human RS virus fusion protein (140,000 daltons) obtained from RS virus A2 strain, a subtype A virus. Control animals were similarly immunized with a placebo immunogen, i.e. PBS.

Serology assays were performed as described in Section 6.1.2, supra, to test the virus neutralization and anti-fusion capabilities of the induced antibodies against both A and B subtypes of human RS virus. Immunization with subtype A RS virus fusion protein induced antibodies which exhibited similiar neutralization and anti-fusion activities against both subtypes A and B of RS virus (data not shown).

All experimental and control animals were challenged intranasally at week 6 with human RS virus as follows: Group 1 received strain A2 (subtype A) 6.2 log 10 PFU; Group 2, Long strain (subtype A) 6.1 log 10 PFU; Group 3, strain 9320 (subtype B) 3.5 log 10 PFU; and Group 4, strain 18537 (subtype B) 5.0 log 10 PFU. At 4 days post-challenge, the lungs were harvested and the virus titer was determined as described above. Results are presented in Table 2.

TABLE 2

PROTECTIVE EFFICACY OF FUSION PROTEIN VACCINE AGAINST VARIOUS SUBTYPES OF RSV

| Group No.[a] | Challenge Virus (Subtype) | Lung Titer (GMT)[b] | |
|---|---|---|---|
| | | Experimental[c] | Control[d] |
| 1 | A2 (A) | 1.1 | 5.0 |
| 2 | Long (A) | 1.1 | 4.0* |
| 3 | 9320 (B) | 1.43 | 5.1* |
| 4 | 18537 (B) | 1.1 | 3.5 |

[a]Experimental animals in each group were immunized at week 0, 2 and 4 with 10 ug of F protein purified from RS virus strain A2, subtype A. Control animals in each group similarly received PBS as immunogen. All animals were challenged at week 6 with RS virus. See text for experimental details.
[b]"Lung Titer (GMT)" represents the geometric mean titer (PFU/gm of tissue) of virus isolated from lung tissue.
[c]N = 5.
[d]N = 3, except * which designated N = 2.

As demonstrated in Table 2, immunization with fusion protein from a subtype A virus strain, induced significant protection against both a homologous subtype A virus and a heterologous sybtype B virus in all cases. Thus it is clear that immunization with F protein from one subtype RS virus confers protection against both subtypes of human RS virus.

6.3. Protection of Baboons

Twelve juvenile baboons were divided into 3 groups of 4 animals each. Animals were injected intramuscularly with 20 ug purified RS virus fusion protein at one month intervals for 3 months as follows: Group 1 received immunogen in PBS; Group 2, immunogen in alum; and Group 3, PBS alone (control group).

Serology assays were performed two weeks after the third immunization as described in Section 6.1.2, supra. Results are presented in Table 3.

At 2 weeks post-immunization, 3-4 animals/group were challenged with 5.32 PFU of Strain A2 RS virus by direct innoculation into the lungs. Lung lavages were assayed at day 2 post-infection. Lung lavages were obtained by direct transfer of media into the lungs and collection by tube aspiration. The virus was titered as described in Section 6.2, supra. Results are also presented in Table 3.

TABLE 3

IMMUNOGENICITY OF RSV FUSION PROTEIN IN BABOONS

| Group No. Immunogen (Adjuvant) | Serology[a] | | | Virus Assay[b] | | |
|---|---|---|---|---|---|---|
| | EIA | Virus Neutralization | Anti-fusion | + | − | TITER |
| Group 1 (PBS) | 5.01 | 2.5 | 1.83 | 3 | 1 | 1.05 |
| Group 2 (ALUM) | 6.0 | 3.34 | 2.56 | 0 | 4 | 0.00 |
| Group 3 | <1.0 | <2.0 | <1.0 | 3 | 0 | 2.14 |

TABLE 3-continued

IMMUNOGENICITY OF RSV FUSION PROTEIN IN BABOONS

| Group No. Immunogen (Adjuvant) | Serology[a] | | Virus Assay[b] | | |
|---|---|---|---|---|---|
| | EIA | Virus Neutralization | Anti fusion | + | − | TITER |

(control)

[a]Assays were performed two weeks after the last (third) immunization. Results represent the geometric mean titer 4 animals expressed in log₁₀ units. (See text for experimental details).
[b]Strain A2 RS virus (5.32 PFU) was inoculated directly into the lungs of 3-4 immunized animals in each group at two weeks post immunization. Lung lavages were assayed at day 2 post-infection. "+" represents the number of animals with detectable RS virus in lung lavages. "−" represents the number of animals without detectable RS virus in lung lavages. "Titer" is expressed as the geometric mean titer (PFU/gm) of tissue of virus isolated from lung tissue.

As shown in Table 3, immunization of juvenile baboons with purified RS virus fushion protein elicited antibodies which were able to neutralize virus and prevent fusion. As further clearly demonstrated, immunized animals were protected against subsequent RS virus infection when alum was used as an adjuvant (Group 2).

In another series of experiments, juvenile baboons were divided into a number of groups and immunized by intramuscular injection of purified RS virus fusion protein as follows: 4 animals received 5 ug of immunogen in alum and 11 animals received 20 ug of immunogen in alum on days 0, 28 and 56; 6 animals received 100 ug of immunogen in alum on day 0, 20 ug on day 28 and 20 ug on day 56. Twelve animals received PBS alone on day 0, 28 and 56 and served as controls. All animals were challenged with $<10^6$ PFU of strain A2 RS virus on day 70 by direct inoculation into the lungs. Lung lavages were collected as described above on days 2, 3 and 4 post-challenge Results from this series of experiments are summarized in Table 4.

TABLE 4

SUMMARY OF BABOON PROTECTION

| Immunogen | RSV Isolation From Lung Lavages[a] | | | |
|---|---|---|---|---|
| | N | (+) | (−) | Titer |
| F (alum) | 21 | 2 | 19 | <0.7 |
| PBS | 12 | 12 | 0 | 3.0 |

[a]"(+)" represents the number of baboons in which RS virus was detected in lung lavage. "(−)" represents the number of baboons in which no RS virus was detected in lung lavage. "Titer" is expressed as the geometric mean titer (PFU/ml of tissue) of virus isolated from lung lavage.

As summarized in Table 4, baboons were efficiently protected against RS virus infection by immunization with RS virus fusion protein. During the course of immunization and subsequent challenge experiments, blood chemistries and hematologic assays showed no sign of adverse reactions throughout the course of the experiments.

6.4. Protection Against Bovine RS Virus

A crude preparation of human RS virus fusion protein (herein termed "crude human RS virus F protein") was prepared as follows: Vero cells infected with RS virus A2 strain were extracted with a solution containing 50 mM Tris; 0.15M NaCl; 1% Triton X-100 and 2% deoxycholate; pH 7.4 (Lysis Buffer). The F protein was obtained from the spent cell culture medium by solubilization of PEG pelleted virus using the Lysis Buffer. The resulting crude preparation was clarified by centrifugation. An immunoaffinity purified preparation was prepared as described in Section 6.1.1.

Fifteen cows were divided into 5 groups of 3 animals each. Animals were injected intramuscularly with human RS virus fusion protein on days 0 and 21 as follows: Group 1 received crude human RS virus F protein (5 ug); Group 2, crude human RS virus F protein (20 ug); Group 3, purified human RS virus F protein, (20 ug); Group 4, a USDA approved bovine RS virus vaccine commercially available from Diamond Scientific Co. (Des Moines, Iowa) (2 ml on days 0 and 21) and Group 5, PBS alone (control).

EIA's were performed on serum samples obtained on days 0, 10, 21 and 33 post-immunization as described in Section 6.1.2., supra, F protein from RS virus strain A2 as antigen. Results are presented in Table 5.

TABLE 5

IMMUNOGENICITY OF RS VIRUS FUSION PROTEIN IN COWS

| Immunogen[a] | Serology (EIA)[b] Day | | | |
|---|---|---|---|---|
| | 0 | 10 | 21 | 33 |
| HRSV F protein (5 ug)* | — | — | 3.6 (2/3) | 5.8 |
| HRSV F Protein (20 ug)* | — | 3.8 (2/3) | 4.2 (3/3) | 6.2 |
| HRSV F protein (20 ug) | — | 3.8 (2/3) | 4.6 (2/3) | 5.9 |
| Diamond Vaccine (BRSV) | 2.2 (1/3) | 3.0 (1/3) | 3.5 (2/3) | 4.7 |
| PBS | — | — | — | — |

[a]Cows were immunized at days 0 and 21 with either crude (*) or immunoaffinity purified F protein and the immunogenicity was compared with that of a commerically available USDA approved BRSV vaccine (Diamond Scientific Co. vaccine). See text for details.
[b]Results represent the geometric mean titer of 3 animals expressed in log₁₀ units. The ratio in the parenthesis is the number of ELISA positive animals. "—" indicates that the titer was not detectable, i.e., less than 1.6.

The data presented in Table 5 shows that the human RS virus fusion protein obtained as described in Section 6.1 and after immunoaffinity purification elicits high levels of antibodies. Comparison with a commercially available bovine RS virus vaccine showed that the human RS virus protein was as immunogenic or more immunogenic in cows than the BRSV vaccine.

The protective immunogenicity of the human RS virus fusion protein against bovine RS virus was investigated in another series of experiments. Twenty five cotton rats were divided into 2 groups of 10 animals each and one group of 5 animals each. Animals were immunized intramuscularly on days 0 and 21 as follows: Group 1 received the commercially available BRSV vaccine (Diamond); Group 2, human RS virus Long strain F and G protein (10 ug each)/Alum (affinity purified F and G proteins were obtained as described in Sections 6.1.1 and 10.1, respectively); and Group 3, PBS/Alum (control). Serum samples were obtained and serological assays were performed as described in Section 6.2, supra, except that BRSV (strain 3758) was used for the neutralization and anti-fusion assays. Results are presented in Table 6.

TABLE 6

PROTECTIVE EFFICACY OF HUMAN RS FUSION PROTEIN AGAINST BOVINE RS VIRUS[a]

| | Serology[b] | | | | | |
|---|---|---|---|---|---|---|
| | EIA Day | | Neutralization Day | | Anti-fusion Day | |
| Immunogen | 21 | 28 | 21 | 28 | 21 | 28 |
| Diamond | 4.2 (10) | 5.3 (6) | n.d. | 2.6 (6) | n.d. | <1:20 (6) |
| F&G/Alum[c] | 6.0 (10) | 7.0 (8) | n.d. | 4.3 (8) | n.d. | 2.2 (8) |
| PBS/Alum | <1:100 | <1:100 | n.d. | <1:20 | n.d. | <1:20 |

TABLE 6-continued
PROTECTIVE EFFICACY OF HUMAN RS FUSION PROTEIN AGAINST BOVINE RS VIRUS[a]

| | Serology[b] | | | | | |
|---|---|---|---|---|---|---|
| | EIA Day | | Neutralization Day | | Anti-fusion Day | |
| Immunogen | 21 | 28 | 21 | 28 | 21 | 28 |
| | (5) | (10) | (4) | | (4) | |

[a]See text for experimental details.
[b]Results represent the geometric mean of 4 to 10 animals expressed in log 10 units. The number in parentheses indicates the number of animals.
[c]The dose was 10 ug of each protein.

As demonstrated in Table 6, human RS virus fusion (and G) protein elicited very high titer of antibodies that showed high neutralizing and anti-fusion activities against BRSV. On the other hand, the Diamond BRSV vaccine elected antibodies that had no detectable anti-fusion activity and significantly lower neutralization activity. Thus, the results presented in Table 6 clearly indicate that human RS virus fusion protein elicits antibodies that neutralize BRSV and prevent fusion induced by BRSV. Hence, the human RS virus fusion protein elicits a protective immune response against BRSV.

6.5. Avoidance of Enhanced Disease

Immunization or vaccination with formalin inactivated RS virus (Lot 100, Pfizer) has been associated with the development of atypical and more severe disease when immunized subjects have been subsequently infected with RS virus. (Kim et al., 1969, Am. J. Epidemol. 89:422-34; Chin et al., 1969, Am. J. Epidemol. 89:449-63). Such potentiation of RS virus infection has been a major hurdle for the development of an efficacious and safe RS virus vaccine formulation for human and animal subjects.

Prince et al. (1985, J. Virol. 57:721-28) developed an animal model for the assessment of the potentiation or enhancement of RS virus induced disease. The cotton rat animal model developed by Prince was employed to investigate whether or not similar potentiation or enhancement of subsequent disease was associated with the use of RS virus F protein as an immunogen according to one embodiment of the present invention. Briefly, cotton rats were immunized by intramuscular injection of either RS virus F protein, with or without Alum as an adjuvant, or one of a variety of immunogens as indicated in Table 7. All animals received three injections either on week 0, 1 and 2 or on week 0, 2, and 4, except for one group which received only one immunization. One to two weeks following the last immunization, animals were challenged with $10^4$–$10^6$ PFU/animal of RS virus. At a 1 and/or 4 days post-challenge, the lungs of the animals were examined for morphological, inflammatory and pathological changes in alveolar ducts and/or alveoli according to the method of Prince et al., supra. The overall pathology of large and small airways of lungs were scored using a scheme ranging from mild (+1), moderate (+2), severe (+3) to very severe (+4). Results are presented in Table 7.

TABLE 7
ENHANCED PATHOLOGY COTTON RAT MODEL: FREQUENCY OF OCCLUDED SMALL AIRWAYS

| Immunogen (Dose)[a] | Sample Challenge | Alveolar and/or Alveoli Pathology[b] | | | | |
|---|---|---|---|---|---|---|
| | | Day | N | + | (%) | Severity |
| Lot-100 (undil) | RSV | 1 | 2 | 1 | (50) | 1.5 |
| Lot-100 (undil) | RSV | 4 | 3 | 2 | (67) | 1.5 |
| RSV-formalin (undil-1:625)*** | RSV | 1 | 18 | 13 | (72) | 2.0 |
| RSV-formalin (undil-1:625)*** | RSV | 4 | 17 | 11 | (65) | 1.5 |
| RSV-live ($10^1$–$10^6$ PFU) | RSV | 1 | 13 | 2 | (15) | 1.0 |
| RSV-live ($10^1$–$10^6$ PFU) | RSV | 4 | 15 | 3 | (20) | 1.0 |
| F (Alum)* (0.2-20 ug) | RSV | 4 | 52 | 0 | 0 | — |
| F (5 ug) | RSV | 1 | 3 | 0 | 0 | — |
| F (0.2-10 ug) | RSV | 4 | 23 | 0 | 0 | — |
| F** (1-20 ug) | RSV | 4 | 11 | 1 | (9) | 0.5 |
| Medium | RSV | 1 | 2 | 0 | | |
| Medium | RSV | 4 | 2 | 1 | (50) | 1.0 |
| PBS | RSV | 1 | 4 | 1 | (25) | 1.0 |
| PBS | RSV | 4 | 22 | 3 | (14) | 1.0 |
| None | RSV | 1 | 3 | 0 | 0 | — |
| None | RSV | 4 | 3 | 0 | 0 | — |
| None* | Medium None | 4 | 3 | 0 | 0 | — |
| None* | None or PBS | 4 | 9 | 0 | 0 | — |

[a]All animals were immunized by a 200 ul intramuscular injection of immunogen three times at weeks 0, 1, and 2, except for those designated * which were immunized at weeks 0, 2 and 4 and  which received a single intramuscular injection at week 0. "*" indicates that the undiluted virus was $10^6$–$10^7$ PFU.
[b]"Day" indicates the day post-challenge on which the pathology of lung avelolar ducts and/or alveoli were evaluated. "N" indicates the total number of animals evaluated. "+" indicates the number of animals in which pathological changes were noted, indicating enhanced or potentiated RS virus induced disease. "(%)" represents the percent of animals in which enhanced RS virus induced disease was observed. "Severity" represents the mean histopathological score on a scale of according to the method of Prince et al., supra 0 to +4)

As demonstrated in Table 7, animals which were immunized with RS virus fusion protein according to one embodiment of the present invention, did not exhibit pathological changes in lung tissues, including alveolar ducts and/or alveoli. On day 4, only 1 out of 86 animals immunized with fusion protein showed less than mild pathological change. On the other hand, of animals immunized with commercially available RS virus vaccine Lot 100 or formalin-inactivated RS virus, greather than 65% of treated animals had mild to moderate pathological deterioration and/or inflammation of lung tissues. Additionally, 20% of animals immunized with live RS virus showed at least mild pathological deterioration and/or inflamation of lung tissues. Thus, the use of RS virus fusin protein according to the present invention avoided the enhancement or potentiation of disease induced by subsequent RS virus infection. Hence the vaccine formulations according to the present invention are both safe and efficacious.

7. Protection of Humans: RS Virus Fusion Protein

FDA approved human phase I clinical studies were conducted to evaluate the safety and immunogenicity of RS virus fusion protein vaccine in human adult volunteers. The fusion protein from the RS virus strain A2, was purified as described in Section 6.1, supra, compounded with alum, and injected intramuscularly in the following doses: Group 1 received 5 ug (N=15), Group 2, 15 ug (N=16); and Group 3, 45 ug (N=9). One month later, 6 volunteers from Group 1 and 7 volunteers from Group 2 were boosted with a repeat injection of the respective amounts of RS virus fusion protein received at the first immunization. The schedule for vaccinations and collection of serum samples from volunteers is illustrated in Table 8.

TABLE 8
DESCRIPTIVE DATA FROM PHASE I CLINICAL TRIAL OF RS VIRUS F PROTEIN IN ADULTS

| Volunteers | | RS Virus F Protein | | | |
|---|---|---|---|---|---|
| | | 5 ug | 15 ug | 45 ug | Total |
| N | | | | | |
| (vax = 1) | | 15 | 16 | 9 | 40 |
| (vax = 2) | | 6 | 7 | | 13 |
| Bleed/Vax timing: | | | | | |
| A(V) | mean | 0 days | 0 days | 0 days | |
| B | mean | 14.1 | 14.1 | 14.0 | |
| C(V) | mean | 32.5 | 28.8 | 30.3 | |
| D | mean | 61.6 | 55.0 | 58.4 | |
| E | mean | 88.7 | 83.0 | 86.4 | |
| F | mean | 166.0 | 161.4 | 165.1 | |

The safety data including clinical data and symptoms reported by immunized human volunteers are summarized in Table 9.

TABLE 9
PHASE-I CLINICAL TRIAL OF RS VIRUS F PROTEIN IN ADULTS: TEMPERATURE AND LOCAL REACTIONS AT VACCINATION SITE OCCURRING WITHIN THE FIRST 24 HOURS POST-VACCINATION

| Type of Reaction | Score | Number of Individuals by Reaction Vaccine: | | | | | | |
|---|---|---|---|---|---|---|---|---|
| | | Primary | | | | Secondary | | |
| | | Dosage: | | | | | | |
| | | 5 ug | 15 ug | 45 ug | All | 5 ug | 15 ug | All |
| Temperature | 0 (≦100° F.) | 15 | 15 | 9 | 39 (100%) | 6 | 7 | 13 (100%) |
| | 1 (>100° F.) | 0 | 0 | 0 | 0 | 0 | 0 | 0 |
| Redness (local) | 0 (≦ none) | 15 | 14 | 9 | 38 (97%) | 5 | 7 | 12 (92%) |
| | 1 (1 cm) | 0 | 1 | 0 | 1 (3%) | 0 | 0 | 0 |
| | 2 (≧2 cm) | 0 | 0 | 0 | 0 | 1 | 0 | 1 (8%) |
| Swelling (local) | 0 | 15 | 14 | 8 | 37 (94%) | 6 | 7 | 13 (100%) |
| | 1 (≦1 cm) | 0 | 0 | 0 | 0 | 0 | 0 | 0 |
| | 2 (≧2 cm) | 0 | 0 | 1 | 2 (6%) | 0 | 0 | 0 |
| Warmth (Local) | 0 | 15 | 15 | 8 | 38 (97%) | 6 | 7 | 13 (100%) |
| | 1 (≦1 cm) | 0 | 0 | 0 | 0 | 0 | 0 | 0 |
| | 2 (≧2 cm) | 0 | 0 | 1 | 1 (3%) | 0 | 0 | 0 |
| Pain (local) | 0 (none) | 10 | 6 | 3 | 19 (49%) | 3 | 3 | 6 (46%) |
| | 1 (touch/movement) | 5 | 6 | 5 | 16 (41%) | 3 | 3 | 6 (46%) |
| | 2 (always) | 0 | 3 | 1 | 4 (10%) | 0 | 1 | 1 (8%) |

As demonstrated in Table 9, the adverse reactions (local reactions) to the immunization were very minimal and/or insignificant. Blood was drawn from the volunteers at specified time intervals and tested for the antibody titer specific to the RS virus protein as described above. Results are presented in Table 10.

TABLE 10
IMMUNOGENICITY OF RS VIRUS F PROTEIN IN ADULTS EIA SEROLOGY*

| Vaccination | Bleed | Geometric Mean Titer (Range) [N] | | |
|---|---|---|---|---|
| | | Group 1 | Group 2 | Group 3 |
| Primary | A | 66.4 (15-176) [n = 15] | 58.9 (21-200) [n = 16] | 90.9 (27-299) [n = 9] |
| | B | 160.8$^a$ (30-328) [n = 15] | 229.0$^a$ (40-965) [n = 16] | 415.3$^a$ (179-700) [n = 9] |
| | C | 141.3$^b$ (33-276) [n = 15] | 199.9$^a$ (46-828) [n = 9] | 386.2$^a$ (153-703) [n = 9] |
| | D | 116.2$^c$ (31-217) [n = 8] | 235.2$^a$ (73-644) [n = 9] | 351.1$^b$ (121-645) [n = 9] |
| | E | 119.4$^c$ (35-195) [n = 9] | 180.2$^a$ (60-493) [n = 9] | 349.0$^b$ (129-705) [n = 9] |
| | F | 106.1 (25-169) [n = 9] | 144.5$^b$ (46-330) [n = 9] | 314.8$^b$ (111-538) [n = 9] |
| Boost | D | 183.4$^b$ (98-302) [n = 6] | 217.7$^a$ (105-117) [n = 7] | |
| | E | 166.7$^b$ (103-352) [n = 6] | 217.6$^a$ (99-658) [n = 7] | |
| | F | 126.1$^c$ (76-234) [n = 6] | 180.2$^b$ (91-691) [n = 7] | |

*EIA titer is expressed as titer (X1000). Values represent geometric mean titer, with the range in parentheses and the number of samples in square brackets.
$^a$Comparison to Bleed A GMT by T test showed significant difference p < 0.001.
$^b$Comparison to Bleed A GMT by T test showed significant difference p < 0.01.
$^c$Comparison to Bleed A GMT by T test showed significant difference p < 0.05.

As shown in Table 10, significantly enhanced quantities of antibodies compared to the pre-existing antibodies were produced in all groups, following the immunization with either 5 or 15 or 45 ug of RS virus F protein. Hence, the RS virus F protein according to one embodiment of this invention, is very immunogenic not only in animals but also in humans.

8. IDENTIFICATION OF NEUTRALIZING AND/OR FUSION EPITOPE[S] OF RS VIRUS FUSION PROTEIN

8.1. General Procedures

The following protocols were used to define an epitope of RS virus fusion protein which elicits both neutralizing and antifusion antibodies.

8.1.1. Protein Immunoblot (Western Blot) Analysis

Fusion protein subunits $F_1$ and $F_2$ were subjected to SDS-PAGE (Laemmli, 1970, Nature, 227:680-685). The separated protein subunits in the gel were electrophoretically transferred to a nitrocellulose sheet using a transfer solution containing 12.1 g Tris-HCl, 56.3 g glycine per 5 liters. The nitrocellulose sheet was air dried. The air-dried nitrocellulose was incubated at 37° C. sequentially with (i) BLOTTO for 15 min., (ii) BLOTTO containing the L4 monoclonal antibody for 15 min., (iii) BLOTTO for 15 min., (iv) BLOTTO containing secondary antiserum for 60 min., and (v) BLOTTO for 15 min.

The secondary antiserum bound to the L4 monoclonal antibody, and was either labeled with horse radish peroxidase or not labeled. If labeled with peroxidase, antibody binding was detected by color development brought about by enzymatic reaction with 0.05% 4-chloronapthol, 0.09% $H_2O_2$ in phosphate buffered saline pH 6.8. If unlabeled, antibody binding was detected by autoradiography following $^{125}$I- protein A binding to the antibodies.

8.1.2. Coupling of Peptides to Keyhole Lympet Hemocyanin (KLH) and Production of Rabbit Antisera A 1 mg/ml KLH solution was prepared as follows: 4 mg of a resuspended ammonium sulfate precipitate of KLH (containing 37 mg of protein/ml) was centrifuged for 5 minutes at 4° C. in a microfuge. The supernatant was discarded and the pellet redissolved in 3 ml of 0.1M $NaHCO_3$. The solution was dialyzed against 0.1M $NaHCO_3$ with 2 changes. The volume of the dialyzed KLH solution was adjusted to 4 ml to make a 1 mg/ml KLH solution.

Four ul of a 1 mg/ml solution of a synthetic polypeptide were added to the KLH solution, and mixed at room temperature for 1 hour. Four ml of 25% aqueous glutaraldehyde were added to the mixture, and mixed for another 24 hours at room temperature. Twenty ul of 25% aqueous glutaraldehyde were again added to the mixture and mixed for a further 72 hours at room temperature. The glutaraldehyde cross-linked synthetic polypeptide—KLH was dialyzed overnight against PBS with several changes of the dialysis buffer.

Rabbits were immunized with 250 ug of protein in complete Freund's adjuvant, and boosted 2-3 times at 2 week intervals with 250 ug of protein in incomplete Freund's adjuvant.

8.1.3. Proteolytic Cleavage of Fusion Protein Trypsin Digestion without L4 Protection Purified fusion protein in 50 mM Tris, pH 7.1, .05% SDS and 0.1% beta-mercaptoethanol was heated for 5 minutes at 100° C. Trypsin was added to the cooled, denatured fusion protein sample and incubated at 37° C. for 2 hours Enzyme to substrate ratios of 1:1000, 1:2500, and 1:5000 were used. Unless otherwise stated, all proteinases are added from a 1 mg/ml stock solution.

Trypsin Digestion with L4 Protection

Equal molar amounts of purified fusion protein and L4 monoclonal antibody were mixed and set on ice for 1 hour. Trypsin was added to the mixture in the presence of 50 mM Tris, pH 7.1, and incubated at 37° C. for 2 hours. An enzyme to substrate ratio of 1:10 was used.

Trypsin/Arg-C Digestions with L4 Protection

Equal molar amounts of purified fusion protein and L4 monoclonal antibody were mixed and set on ice for 1 hour. Trypsin digestion at an enzyme to substrate ratio of 1:10 was carried out as described in Example 2.2. The trypsin-digested fusion protein was heated for 5 minutes at 100° C., cooled and digested further by Arg-C at enzyme to substrate ratios of 1:2, 1:5, 1:10 at 37° C. for 2 hours.

Arg-C/Arg-C Digestions with L4 Protection

Equal molar amounts of purified fusion protein and L4 monoclonal antibody were mixed and set on ice for 1 hour. A first Arg-C digestion of the mixture at an enzyme to substrate ratio of 1:3 was performed in the presence of 20 mM $NH_4HCO_3$ for 2 hours at 37° C. Then the reaction mixture was reduced by adding 2-mercaptoethanol to a final concentration of 0.1% and heated for 5 minutes at 100° C. After cooling, a second Arg-C digestion at an enzyme to substrate ratio of 1:6 for 2 hours at 37° C. was carried out.

Lys-C/Arg-C Digestions with L4 Protection

The same protocol was followed as in Example 2.4 above except that Lys-C at an enzyme to substrate ratio of 1:2 was used in the first digestion.

8.1.4. Dot Blot Analysis

Dot blot analysis was performed on synthetic polypeptides as follows:

Polypeptides (up to 20 ug) were spotted on the nitrocellulose sheets. The nitrocellulose sheet was air dried. The air-dried nitrocellulose was incubated at 37° C. sequentially with (i) BLOTTO (5% Carnation ™ instant milk in phosphate buffered saline pH 6.8) for 15 min., (ii) BLOTTO containing the L4 monoclonal antibody for 0.25-72 hrs, (iii) BLOTTO for 15 min., (iv) BLOTTO containing secondary antiserum for 60-120 min., and (v) BLOTTO for 15 min.

The secondary antiserum bound to the L4 monoclonal antibody, and was either labeled with horse radish peroxidase or not labeled. If labeled with peroxidase, antibody binding was detected by color development brought about by enzymatic reaction with 0.06% 4-chloronapthol, 0.3% $H_2O_2$ in phosphate buffered saline pH 6.8. If unlabeled, antibody binding was detected by autoradiography following $^{125}$I- protein A binding to the antibodies.

8.2. Mapping by Defined Proteolytic Cleavage

Figure 3:
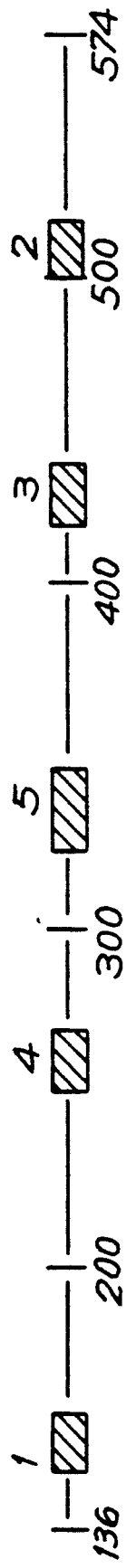

In order to map the $F_1$ subunit of the RS virus fusion protein, synthetic polypeptides were prepared corresponding to various regions of the $F_1$ subunit as depicted in FIG. 3 and designated synthetic polypeptides (sp) sp1 through sp5. These sp were coupled to KLH as described supra and employed separately to immunize rabbits. Five corresponding rabbit antisera were obtained designated anti-sp1 through anti-sp5. All five antisera were reactive with the $F_1$ subunit as well as with the particular sp used as immunogen.

The purified RS virus fusion protein was then subjected to defined proteolytic cleavage as described in detail Section 7.1.3. The cleaved protein fragments were separated by SDS-PAGE to determine molecular weight and analyzed by Western blot analysis for ability to bind to the L4 monoclonal antibody as well as to the antisera raised against the synthetic polypeptides. The position of a given proteolytic fragment within the fusion protein sequence was deduced from the reactivities with each of the antisera. Results are tabulated in Table 11 (A-E) and summarized in FIG. 4.

TABLE 11
MAPPING AND ANTIGENICITY OF PEPTIDE FRAGMENTS OF F PROTEIN

A. Trypsin Digestion of F Protein

| Fragment | I | II | III | IV | V | VI |
|---|---|---|---|---|---|---|
| Probe | 28K-1 | 25K-1 | 24K | 23K | 15K | 14K |
| L4 | + | + | + | + | − | + |
| anti-sp (1) | + | + | + | + | + | − |
| anti-sp (4) | + | + | + | + | + | − |
| anti-sp (5) | − | − | + | − | − | − |
| Predicted Amino Acid Position[b] | 137–394 | 137–364 | 137–359 | 156–364 | 137–272 | |

B. Trypsin Digestion of L4-Protected F Protein

| Fragment | VII | VIII | III |
|---|---|---|---|
| Probe | 28K | 26K | 24K |
| L4 | + | − | + |
| anti-sp (1) | − | − | + |
| anti-sp (2) | + | + | − |
| anti-sp (4) | − | − | + |
| Predicted Amino Acid Position[d] | 272–520 | 336–574 | 137–359 |

C. Trypsin Digestion of L4-Protected F Protein Followed By Arg-C Digestion

| Fragment | III | IV | IX | V |
|---|---|---|---|---|
| Probe | 24K | 23K | 20K | 15K |
| L4 | + | + | + | − |
| anti-sp (4) | + | + | + | + |
| Predicted Amino Acid Position[c] | 137–359 | 156–364 | 156–336 | 137–272 |

D. Arg C Digestion of F Protein

| Fragment | X | XI | XII | XIII | XIV |
|---|---|---|---|---|---|
| Probe | 25K | 23.5K | 21K | 14K | 13K |
| L4 | + | − | + | + | + |
| anti-sp (2) | − | + | − | − | − |
| anti-sp (4) | − | − | + | − | − |
| anti-sp (5) | − | + | − | − | − |
| Predicted Amino Acid Position | 282–507 | 336–553 | 235–429 | | |

E. Lys C Digestion of L4 Protected F Protein Followed By Arg C Digestion

| Fragment | X | XV | XI | XII | XVI | XVII | XVIII |
|---|---|---|---|---|---|---|---|
| Probe | 25K | 25K | 23.5K | 21K | 16K | 14K | 13K |
| L4 | + | − | − | + | − | + | + |
| anti-sp (2) | − | + | + | − | − | − | − |
| anti-sp (4) | − | − | − | + | + | − | − |
| anti-sp (5) | − | − | − | − | − | − | − |
| Predicted Amino Acid Position | 282–507 | 327–553 | 156–336 | 235–429 | 137–282 | 272–399 | 282–399 |

Figure 4:
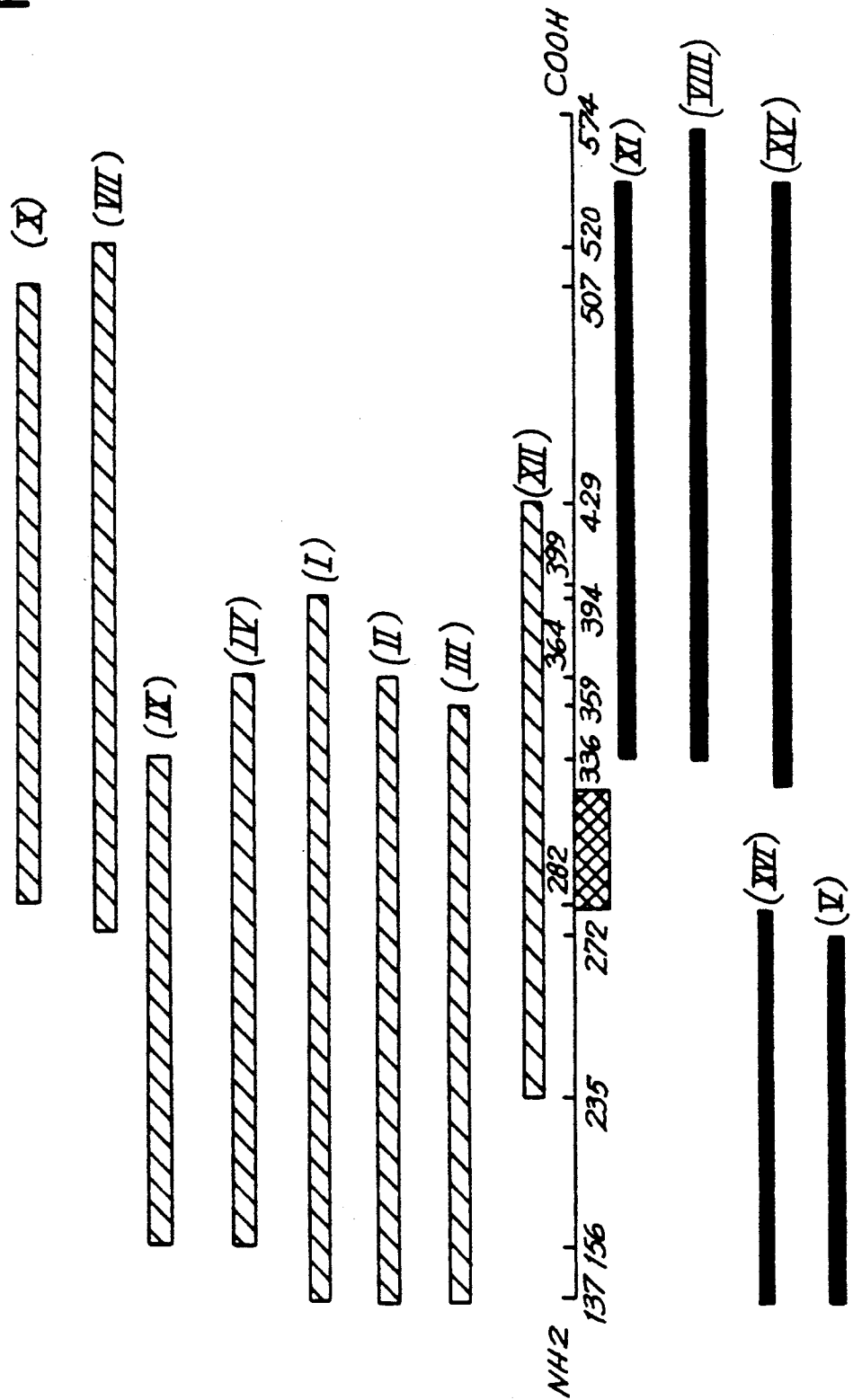
FIG. 4 shows the positions of proteolytic fragments of the fusion protein on a linear map of the $F_1$ subunit.

[a]The Roman Numerals identify the fragments shown in FIG. 4. Approximate molecular weight (daltons) of cleavage fragments are indicated under Roman Numerals.
[b]The predicted amino acid positions of the various fragments were deduced from their reactivity with the anti-synthetic polypeptide sera as well as the known amino acid specificities of the proteases.

Table 11 (A–E) shows the fragments which were derived by the five proteolytic cleavage protocols along with the reactivity to the monoclonal and polyclonal antisera. FIG. 4 consolidates the data of Table 11 (A–E), and shows the position of all of the fragments identified in a linear map. The fragments which reacted with the L4 monoclonal antibody are show as shaded bars and those which did not react are shown in sold bars. The cross-hatched area present in all fragments reactive with L4 monoclonal antibody spans amino acid residues 283–327.

8.3. Mapping by Expression of Protein Fragments

Figure 5:
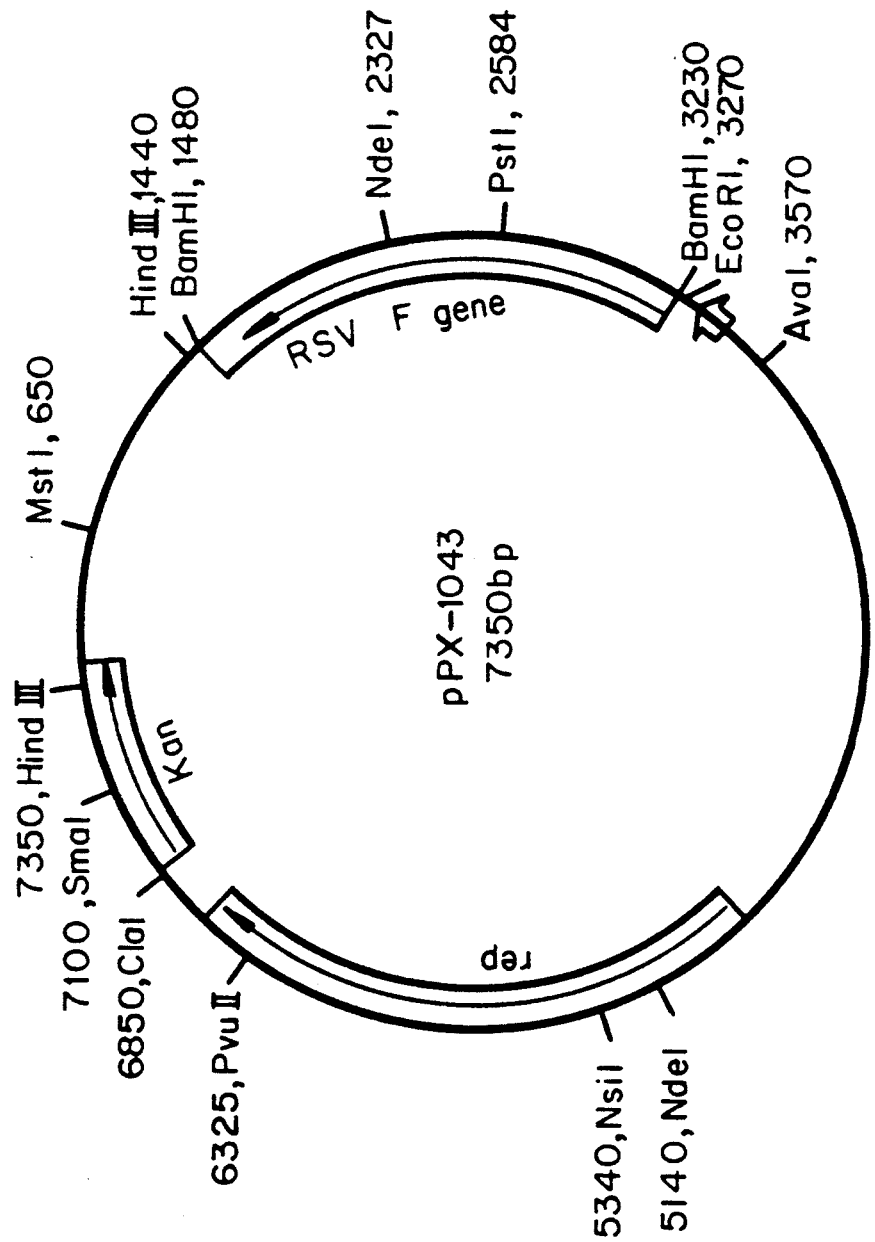
FIG. 5 is a diagramatic representation of an *E. coli* recombinant vector containing the complete nucleotide sequence of the RS virus fusion protein gene.

The cDNA substantially as depicted in FIG. 1 containing the complete nucleotide sequence of the fusion protein gene was cloned into *E. coli* plasmid vector pG103 at the BamHI site. FIG. 5 illustrates the resultant recombinant plasmid pPX1043.

The cDNA substantially as depicted in FIG. 1 containing the complete nucleotide sequence of the fusion protein gene was cloned into *E. coli* plasmid vector pBR322 at the BamHI site. The resultant plasmid was designated pBR322-F. Regions of the fusion protein gene were excised from pBR322-F by restriction endonuclease digestion and ligated into the *E. coli* expression vector pUC19 (Yanish-Perron et al., 1985, Gene 33:103–19). Table 12 shows the restriction sites used, the nucleotide sequences of the fusion protein gene within the restriction fragments and the amio acids encoded by these nucleotide sequences. Each of these DNA fragments was cloned into the *E. coli* expression vector pUC19 in the polylinker region such that the sequences were in frame with the lac Z gene initiation codon. The amino acid sequences encoded by the recombinant DNA molecules at and near the junctions of the vector plasmid and the cloned fusion protein gene fragments are shown in FIG. 6. Since coding sequences of the fusion protein were inserted into the lac Z gene of the pUC19 vector, some amino acids from the lac Z protein as well as some amino acids encoded by the polylinker are included in the recombinant proteins.

TABLE 12
FRAGMENTS OF FUSION PROTEIN GENE CLONED INTO THE pUC19 EXPRESSION VECTOR

| Construction | Recombinant Protein | Restriction Sites Used[a] | Nucleotide Boundaries[b] | Amino Acid Boundaries |
|---|---|---|---|---|
| cF3 | F3 | HpaI-BamHI | 769–1737 | 253–574 |
| cF4 | F4 | PstI-NsiI | 646–1479 | 212–490 |
| cF7 | F7 | PstI-TaqI | 646–1102 | 212–363 |
| cF8 | F8 | PstI-HincII | 646–1165 | 212–384 |
| cF10 | F10 | PstI-NdeI | 646–907 | 212–298 |
| cF11 | F11 | NdeI-NscI | 908–1479 | 299–490 |

[a]A clone of the RSV fusion protein gene was cleaved with the indicated combinations of restriction endonucleases to generate RSV fragments for subsequent cloning into the expression vector pUC19. The nucleotides included within these restriction fragments are indicated along with the predicted amino acids which were expressed.
[b]Nuclestide 1900 is the beginning of the synthetic BamHI linker. Nucleotides 1742–44 is a translation termination signal (TAA) so that amino acid 574 is a terminal amino acid.

Figure 7:
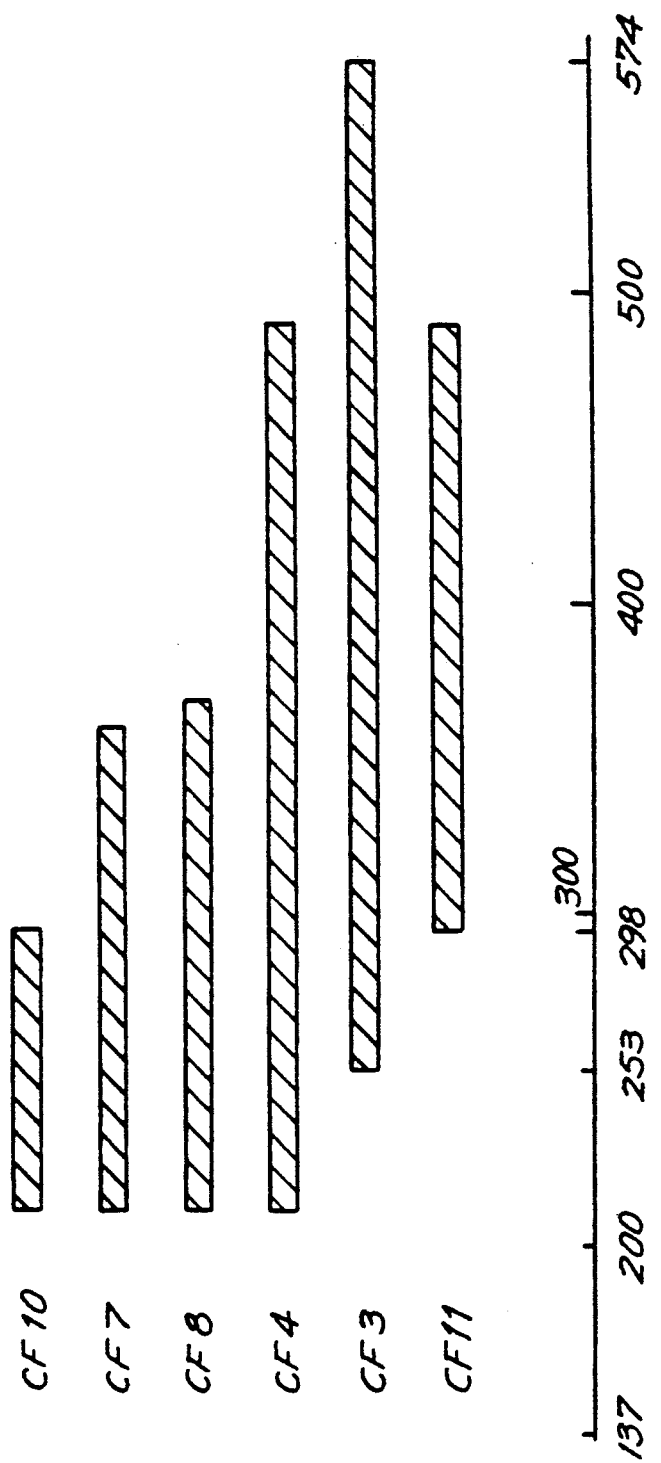
FIG. 7 shows the positions of the recombinant proteins on a linear map of the $F_1$ subunit. The fragments shown in shaded bars were reactive with the L4 monoclonal antibody and those shown in solid bars were non-reactive with the L4 monoclonal antibody.

Six recombinant proteins, designated F3, F4, F7, F8, F10, and F11, corresponding to proteins encoded by construction cF3 (also designated as plasmid pPX-1029), cF4, cF7, cF8, cF10 and cF11, were expressed in *E. coli* as demonstrated by reactivity to polyclonal rabbit antiserum to the native fusion proteins by Western blot analysis as described supra. All of the recombinant proteins except F11 reacted with the L4 monoclonal antibody by Western blot analysis. FIG. 7 shows a diagramatic scheme of the L4 reactive and L4 non-reactive recombinant proteins. As illustrated in FIG. 7, the RS virus fusion protein sequence common to all of the recombinant proteins which are reactive with the L4 monoclonal antibody is defined by residues 253 to 298.

8.4. Mapping by Synthetic Peptides

Four synthetic polypeptides were prepared which corresponded to the amino acid residues 299–315, 294–315, 289–315, and 283–315 of the RS virus fusion protein respectively. The exact sequences of these four synthetic polypeptides are shown in Table 13.

TABLE 13

SEQUENCE OF SYNTHETIC POLYPEPTIDES TESTED FOR REACTIVITY
WITH THE L4 MONOCLONAL ANTIBODY

| Peptide | Sequence[a] | Reactivity with L4 |
|---|---|---|
| 299–315 | YVVQLPLYGVIDTPCWK | − |
| 294–315 | EEVLAYVVQLPLYGVIDTPCWK | + |
| 289–315 | MSIIKEEVLAYVVQLPLYGVIDTPCWK | + |
| 283–315 | QQSYSIMSIIKEEVLAYVVQLPLYGVIDTPCWK | + |

[a]Sequences are given by the standard single letter amino acid code.

The polypeptides were spotted on nitrocellulose sheets and tested for reactivity with the L4 monoclonal antibody by dot blot analysis (see Section 7, supra).

Results obtained are illustrated in FIG. 8. As demonstrated in FIG. 8, peptide 299–315 did not react with the L4 monoclonal antibody whereas polypeptides 294–315, 289–315 and 283–315 did, indicating that a neutralizing and fusion epitope resides between residues 283–298 and can be as small as 294–299. The reasons why the minimum region is set at 294–299 rather than 294–298 is because generally a stretch of at least six amino acids is necessary to form an epitope.

9. Immunogenicity of Modified RS Virus Fusion Protein

9.1. Conformational Modification

Crosslinking experiments demonstrated that the RS virus fusion protein exists as a dimer (140,000 daltons) on the surface of virus infected cells and in substantially pure preparations. In order to investigate the potential effects of protein conformation on the vaccine utility, the quartenary structure of the F protein was modified and resultant effects on immunogenicity evaluated.

A monomeric F protein (70,000 daltons) was obtained from substantially pure F protein by treating the F protein at 100° C. for two minutes or by treatment with 99.9% acetonitrile /0.1% TFA. The immunogenicity of dimeric and monomeric forms was tested in cotton rats. Experimental details and results are presented in Table 14.

TABLE 14

| IMMUNOGENICITY OF RSV-F PROTEIN: EFFECT OF PROTEIN CONFORMATION[a] | | | | |
|---|---|---|---|---|
| Immunogen* | Dose & Route ug (times) | N | EIA log 10 | Neut. Titer log 10 |
| F-dimer | 5 (3× IM) | 15 | 5.7 | 3.8 |
| F-monomer | 5 (3× SC) | 5 | <2.0 | <1.7 |

*The monomeric form was derived from native dimeric form of the F protein by heat treatment. After the treatments, cotton rats were immunized (intramuscular or subcutaneous) 3 times with the indicated immunogens at 2 week intervals and at week 6. Serum was collected and assayed for their titers.

The total neutralizing antibody titers were found to be 100-1000 fold less in the group that received the monomeric form, prepared by heat treatment.

9.2. Deacylated Fusion Protein

In order to determine the effect of covalently attached fatty acid on the immunogenicity of RS virus, the fusion protein was deacylated using hydroxylamine (1M for 4 hours at room temperature) and the efficacy of the deacylated protein was compared to that of F protein. Experimental details and results are presented in Table 15.

TABLE 15

| IMMUNOGENICITY AND PROTECTIVE EFFICACY OF F PROTEIN: EFFECT OF FATTY ACID DEACYLATION[a] | | | | | | | |
|---|---|---|---|---|---|---|---|
| Immunogen | | | Pre-challenge GMT | | RSV isolation and titers from lungs[b] | | |
| Type | Amount (ug) | N | EIA-F | Neut (A2) | (+) | (−) | GMT |
| F | 0.5 | 5 | 156,000 | 233 | 5 | 0 | 3.36 |
| | 5.0 | 3 | 163,000 | 429 | 2 | 1 | 2.04 |
| deacylated F | 0.5 | 6 | 170,000 | 231 | 5 | 1 | 3.31 |
| | 5.0 | 6 | 363,000 | 510 | 6 | 0 | 3.20 |
| PBS | 0.0 | 6 | <100 | <20 | 6 | 0 | 4.32 |

[a]Cotton rats were immunized with the indicated immunogens at week 0, 2 and 4. At week 6, they were challenged with RSV/A2 virus intranasally. Serum was collected from the day of challenge and assayed.

[b]"+" represents the number of animals with detectable RS virus in their lungs at 4 day post-challenge. "−" represents the number of animals without detectable RS virus in their lungs at 4 days post-challenge. GMT titers are expressed as PFU/GM tissue.

Experimental results indicate that the protective efficacy of the deacylated F protein at 5 ug dose was reduced compared to the acylated F protein.

10. Protection of Animals: RS Virus G Protein

10.1. Isolation of G Protein

Substantially pure RS virus G protein suitable for use as an immunogen in a subunit vaccine formulation was prepared essentially according to the method of Walsh et al., 1984, J. Gen. Virol. 65:761-67.

10.2. Passive Protection

Rabbits were immunized using the affinity purified G protein with an intramuscular injection of 2.4 ug of RS virus G protein in Freund's Complete Adjuvant at week 0 and with 4.8 ug of G protein in Freund's Incomplete Adjuvant at weeks 4 and 8. Animals were exsanguinated on week 17. The IgG fractions of sera from the G-immunized rabbits and from a control group of non-immunized rabbits were obtained using a protein A Sepharose TM column.

Twenty cotton rats were divided into 3 groups of 4 animals each and two groups of 5 and 3 animals each. The animals were passively immunized by intraperitoneal injection as follows: Group 1 received 4.12 mg of rabbit anti-G IgG; Group 2, 1.03 mg of rabbit anti-G IgG; Group 3, 4.28 mg of normal rabbit IgG; Group 4, 1.07 mg of normal rabbit IgG; and Group 5 (control), an equivalent volume of PBS. Twenty-four hours post-immunization, animals were challenged with 5.5 log10 PFU RS virus Long strain. Lungs were harvested on day 4 post-challenge. The presence and/or quantity of RS virus in lung tissues was determined as described above. Serum samples were collected and assays were conducted as described above. Results are presented in Table 16.

TABLE 16
PROTECTIVE EFFICACY OF PASSIVE IMMUNIZATION OF ANTI-G ANTIBODIES

| Amount of IgG Administered[a] | Serology[b] | | Virus Assay[c] | | |
|---|---|---|---|---|---|
| | EIA | Virus Neutralization | + | − | TITER |
| Anti G-IgG 4.12 mg | 5.5 | 3.3 | 0 | 4 | ≦1.0 |
| Anti G-IgG 1.03 mg | 4.8 | 3.0 | 0 | 4 | ≦1.0 |
| Normal IgG 4.28 mg | 1.0 | 2.0 | 5 | 0 | 4.5 |
| Normal IgG 1.07 mg | 1.0 | 2.0 | 3 | 0 | 4.9 |
| none (PBS) | 1.0 | 2.0 | 4 | 0 | 5.0 |

[a]Cotton rats were passively immunized using an intraperitoneal injection of rabbit immunoglobulin elicited using purified G protein from RS virus Long stain. The number of animals in each group was four, except those which received 4.28 mg normal rabbit IgG (5 animals) and 1.07 mg normal rabbit IgG (3 animals).
[b]Assays were performed on serum samples obtained on the day of challenge (see text for details). Results represent the geometric mean titer for 3-5 animals expressed in $\log_{10}$ units (EIA) and $\log_{10}$ units/ml serum (Virus Neutralization Assay).
[c]Long strain RS virus 5.5 log 10 PFU was inoculated intranasally (IN) into the passively immunized animals at 24 hours post-immunization and lungs were harested at 4 days post-challenge. Virus was isolated from the lung tissues. "+" indicates the number of animals in each group in which virus was detectable in lungs. "−" indicates the member in which no virus was detected. "Titer" represents the geometric mean titer (PFU/gm of tissue) of virus isolat ed from lung tissue.

As demonstrated in Table 16, passive administration of rabbit antibody induced by purified G protein from RS virus was efficacious in protecting cotton rats against infection by homologous RS virus.

10.3. Active Immunization and Protection

Thirty seven cotton rats were divided into 3 groups of 12-13 animals each. One group was then further subdivided into 4 groups of 3 animals each, thus forming 6 groups. All animals in all groups, except Group 6, were immunized by intramuscular injection of 10 ug of RS virus G protein, obtained as described in Section above, in different adjuvants as follows: Group 1 received three injections at weeks 0, 2 and 4-5 of G protein in PBS; Group 2, three injections at weeks 0, 2 and 5 of G protein in Alum; Group 3, two injections at weeks 0 and 5 of G protein in Alum; Group 4, three injections at weeks 0, 2 and 5 of G protein in ISCOM; and Group 5, two injections at weeks 0 and 5 of G protein in ISCOM. Group 6, the control group, received three injections at weeks 0, 2 and 4 of an equivalent volume of PBS alone. Between weeks 6 and 7, all animals were challenged intranasally with 4.0-5.0 log 10 PFU RS virus Long strain. Serum samples were collected on the day of challenge and assayed as described above in Section 6.2, supra. The presence and-/or quantity of RS virus in lung tissues was determined at 4 days post-challenge as described above. Results are presented in Table 17.

TABLE 17
IMMUNOGENICITY AND PROTECTIVE EFFICACY OF RS VIRUS G PROTEIN

| Group No. | Immunogen (Adjuvant)[a] | N | EIA | Neutralization | Serology[b] Virus Assay[c] | | |
|---|---|---|---|---|---|---|---|
| | | | | | N | + | − | GMT |
| 1 | (PBS) | 12 | 3.4 | 4.0 | 6 | 1 | 5 | 1.4 |
| 2 | (Alum) | 3 | 6.1 | 5.9 | 3 | 0 | 3 | <1.0 |
| 3 | (Alum) | 3 | 6.3 | 5.3 | 3 | 0 | 3 | <1.0 |
| 4 | (ISCOM) | 3 | 6.4 | 5.7 | 3 | 0 | 3 | <1.0 |
| 5 | (ISCOM) | 3 | 6.3 | 5.3 | 3 | 0 | 3 | <1.0 |
| 6 | PBS | 13 | <1.0 | <2.0 | 13 | 13 | 0 | 4.3 |

[a]In all cases, the immunogen was 10 ug G protein in an adjuvant as indicated.
[b]Assays were performed on serum samples obtained on the day of challenge. Results represent the geometric mean titer expressed in $\log_{10}$ units.
[c]Virus was isolated from the lung tissues. "N" indicates the number of animals examined. "+" indicates the number of animals in each group in which virus was detectable. "−" indicates the member in which no virus was detected. "Titer" represents the geometric mean titer (PFU/gm of tissue) of virus isolated from lung tissue.

As illustrated in Table 17, active immunization of cotton rats with G protein obtained from RS virus Long strain induced a significant immune response as demonstrated by high titers of anti-G antibody (EIA assay) that were capable of neutralizing RS virus Long strain (Neutralization assay). Most importantly, when immunized animals were challenged with RV virus Long strain, they were effectively protected against such infection as compared to control animals.

11. IMMUNOGENICITY OF RS VIRUS G PROTEIN EXPRESSED IN RECOMBINANT VECTORS

A recombinant vector expressing the RS virus Strain A2 G protein was prepared. Plasmid pPL-lambda (pPL), which carries the $P_L$ promoter and the N gene on a 1215 bp segment of the bacgeriophage lambda genome was purchased from Pharmacia Fine Chemicals (Piscataway, NJ). A unique HpaI site in the N gene is located 321 bp downstream from the start of $P_L$ transcription. Sequences inserted into this restriction site will this be regulated by the $P_L$ promoter. An expression vector plasmid pPX1600 was constructed by inserting a synthetic ologinucleotide sequence into the HpaI site of the pPL plasmid. This oligonucleotide contained a translation termination codon in frame with the N coding sequences followed by translation initiation signals (Shine-Dalgarno box plus ATG) and unique restriction sites (NcoI, StuI, EcoRV) for insertion of heterologous DNA sequences in frame with the synthetic ATG. A full length cDNA corresponding to the G glycoprotein gene that was flanked by BamHI linkers (Elango et al., 1980, Proc. Nat'l Acad. Sci. USA 83:1906-10) was cloned into the BamHI site of pBR322. After BamHI digestion, the RS virus gene encoding the G protein was excised from pBR322, filled with the Klenow fragments of DNA polymerase I, and blunt end ligated to StuI-cleaved pPX1600. Following transformation of E. coli (N99cI+ strain), the plasmid pPX1044 was isolated (FIG. 9). In this plasmid, the RS virus G encoding sequence was in the correct orientation and reading frame for $P_L$-directed expression by readthrough from the synthetic ATG.

Plasmid pPX1044 was introduced into Salmonella typhimurium (LB50150) cells by the $CaCl_2$ procedure. The transformed cells were grown to late log phase and the expressed RS virus G protein was purified by an immunoaffinity method using L9 monoclonal antibody (Walsh and Hruska, 1983 J. Virol. 47:171-177). The recombinant non-glycosylated G protein produced significant neutralization titers (3.7 logs/ml against Long srain) in rabbits, following 4 immunizations with 10 ug in the presence of Freund's adjuvant. A similar neutralizing antibody response was elicited in cotton rats after 3 immunizations with 5ug of the recombinant non-glycosylated G protein. Hence, the bacterially derived recombinant G is immunogenic and the antibodies produced against the recombinant G are functional and therefore will be protective against RS virus infection.

12. CELL-MEDIATED IMMUNOLOGICAL ASPECTS OF RS VIRUS VACCINE

The data presented in this application demonstrate that immunization with RSV glycoprotein(s) either F protein alone or in combination with G protein, induces circulating antibodies that are functional and protective. In addition to this antibody response, cell mediated immunity may be of importance for the protective efficacy. Indeed, several studies have shown that many viral infections are associated with the induction of cytotoxic T cells which recognize viral glycoproteins. Cytotoxic T cells against RS virus have been described in mouse and humans (Taylor, et al., 1984, Infect. Immun. 43:649-55; Bangham et al., 1985, J. Virol 56:55-59; Bangham et al., 1986, Proc. Nat'l Acad Sci. USA 83:9183-87). Moreover, it has been shown that passive transfer of T cells from RSV-primed mice can clear a presistent RSV infection when the cells are administered to athymic nude mice (Cannon et al., 1987, Immunol. 62:133-38). In order to investigate whether immunization with RS virus F protein could induce cytotoxic T cell responses, mice were immunized with purified RS virus F protein and immune-stimulated effector T cells were assayed in vitro. Responses in animals immunized with live RS virus were also examined. In practice, 36 mice were divided into 4 groups and animals were immunized at 0 and 2 months as follows: Group 1 received $2 \times 10^6$ TCID50 Long strain RS virus intranasal and intraperitoneal injections respectively; Group 2, 20 ug RS virus F protein (in Alum) via intranasal injections; Group 3, 20 ug RS virus F protein (in Alum) via intramuscular injections; and Group 4, were a non-immunized control group. Three week after the last booster injection, animals were sacrificed and spleens were harvested. Effector T cells were obtained from the spleens and were re-stimulated in vitro with either peritoneal exudate cells (PEC) or spleen cells infected with RS virus. Cytotoxic T cells were tested using a Cr-51 release assay (Bangham et al., 1985, J. Virol. 56:55-59). The results are presented in Table 18.

TABLE 18

| | | \% Cr Release From Target Cellsb | | | | | |
|---|---|---|---|---|---|---|---|
| | CTL RESPONSE INDUCED BY RSV-F PROTEIN | | | | | | |
| | In Vitro | | | | | | |
| Group No.[a] | Stimulation | RSV + PEC | | BCH-4 | | RSV − PEC[c] | |
| | | 40:1 | 10:1 | 40:1 | 10:1 | 40:1 | 10:1 |
| 1 | RSV + PEC | 10.1 | 3.9 | 6.2 | −4.2 | 0.8 | 0.2 |
| | RSV + spleen | 23.8 | 10.0 | 15.2 | −2.0 | −0.2 | 1.1 |
| | None | −0.2 | — | −0.2 | — | −0.3 | — |
| 2 | RSV + PEC | 12.4 | 4.0 | 9.2 | −2.6 | 0.97 | −0.8 |
| | RSV + spleen | −0.2 | −0.2 | −1.4 | −0.6 | −0.1 | 1.5 |
| | None | −0.7 | — | 1.6 | — | −0.8 | — |
| 3 | RSV + PEC | 2.4 | 2.4 | 8.4 | 1.2 | 0.4 | −0.8 |
| | RSV + spleen | −0.3 | −0.1 | −6.0 | −5.3 | 0.8 | −1.6 |
| | None | −0.2 | — | 0.2 | — | −5.8 | — |
| 4 | RSV + PEC | 0.4 | — | 5.8 | — | 0.5 | — |
| | RSV + spleen | −0.4 | — | 1.0 | — | −0.2 | — |
| | None | −1.5 | — | 0.6 | — | 0.2 | — |

[a]See text for experimental details.
[b]Target cells were BCH4 cells (a persistently RSV Long strain infected Balb/c fibroblast cell line), RSV infected peritoneal exudate cells (PEC) and uninfected PEC cells.
[c]The ratio indicates the ratio of effector: target cells.

Significant levels of RS virus specific cytotoxic T cells were induced following immunization with RS virus F protein (IP/IP) i.e. Group 2 and with RS virus (IN/IP), i.e., Group 1. No significant T cell response was observed in animals which received RS virus F protein via an intramuscular route, i.e., Group 3 or in control animals, i.e., Group 4. The induction of cytotoxic T cells thus depends upon the route of inoculation, proteins versus live virus and the cells used for restimulation. Purified F protein of RSV is able to induce not only humoral but also cellular immunity.

13. DEPOSIT OF MICROORGANISMS

Many polynucleotide sequences may be used to practice the present invention. E. coli strain JM83 carrying plasmid pPX1043 which comprises the complete RS Virus fusion protein gene and an E. coli strain JM103 carrying plasmid pPX1029 have been deposited with the Agricultural Research Culture Collection (NRRL) Peoria, IL and have been assigned accession numbers NRRL B-18254 and NRRL B-18255 respectively. E. coli strain N99cI+ carrying plasmid pPX1044 has also been deposited with the Agricultural Research Culture Collection (NRRL), Peoria, Ill. and has been assigned accession number B-18419.

The present invention is not to be limited in scope by the microorganisms deposited, since the deposit of microorganisms is only intended as a single illustration of one aspect of the invention.

Many variations of this invention as herein set forth may be made without departing from the spirit and scope thereof. Such variations are intended to fall within the scope of the appended claims. The specific embodiments described are given by way of example only, and the invention is limited only by the appended claims.

What is claimed is:

1. A method for protecting a primate from a disease induced by Respiratory Syncytial virus, comprising: administering to the primate an effective amount of a vaccine formulation which comprises a substantially pure polypeptide which is a human Respiratory Syncytial virus fusion protein, characterized by purity of greater than 75% by weight, a molecular weight of about 140,000 daltons, and having a native dimeric form, in combination with an adjuvant suitable for administration to the primate.

2. A method for protecting a human from disease induced by Respiratory Syncytial virus, comprising: administering to the human an effective amount of a vaccine formulation which comprises a substantially pure polypeptide which is a human Respiratory Syncytial virus fusion protein, characterized by purity of greater than 75% by weight, a molecular weight of about 140,000 daltons, and having a native dimeric form, in combination with an adjuvant suitable for administration to the human.

3. The method according to claim 2, in which the adjuvant is alum.

* * * * *